United States Patent [19]
Studier et al.

[11] Patent Number: 5,824,528
[45] Date of Patent: Oct. 20, 1998

[54] CLONING AND EXPRESSION OF AUTOGENES ENCODING RNA POLY, ERASES OF T7-LIKE BACTERIOPHAGES

[75] Inventors: F. William Studier, Stony Brook; John W. Dubendorff, Sound Beach, both of N.Y.

[73] Assignee: Associated Universities, Inc., Washington, D.C.

[21] Appl. No.: 292,081

[22] Filed: Aug. 15, 1994

Related U.S. Application Data

[63] Continuation of Ser. No. 879,687, May 5, 1992, abandoned, which is a continuation-in-part of Ser. No. 876,972, May 1, 1992, abandoned.

[51] Int. Cl.⁶ .............................. C12N 1/21; C12N 9/12; C12N 15/54; C12N 15/70
[52] U.S. Cl. ................. 435/194; 435/252.3; 435/252.33; 435/320.1; 536/23.2; 536/23.72
[58] Field of Search ............................... 536/23.2, 23.72; 435/232, 320.1, 194, 252.3, 252.33

[56] References Cited

U.S. PATENT DOCUMENTS 4,952,496  8/1990  Studier et al. ........................ 435/91.41

FOREIGN PATENT DOCUMENTS

WO9426911  11/1994  WIPO ............................ C12N 15/63

OTHER PUBLICATIONS

X. Chen, et al., "A Self–Initiating Eukaryotic Transient Gene Expression System Based on Cotransfection of Bacteriophage T7 RNA Polymerase and DNA Vectors Containing A T7 Autogene", Nucleic Acids Research, 1994, vol. 22, No. 11, pp. 2114–2120.
Benton et al. (1990), *Mol. Cell. Biol.* 10:353–360.
Blackman, K., et al. (1976), *Proc. Nat. Acad. Sci., U.S.A.* 73:4174–41780.
Birnboim, H.C. and Doly, J. (1979), *Nucleic Acids Res.* 7:1513–1523.
Bolivar, F., et al. (1977), *Gene* 2:95–113.
Butler and Chamberlin (1982), *J. Biol. Chem.* 257:5772–5778.
Calos, M.P. (1978), *Nature (London)* 274:762–765.
Casababan, M.J., et al. (1983), *Methods Enzymol.* 100:293–308.
Chamberlin, M., et al. (1970), *Nature (London)* 228:227–231.
Chang, A.C.Y. and Cohen, S.N. (1978), *J. Bacteriol.* 134:1141–1156.
Chapman, K.A. and Burgess, R.R. (1987), *Nucleic Acids Res.* 16:5413.
Chapman, K.A. and Wells, R.D. (1982), *Nucleic Acids Res.* 10(20):6331.
Chen, E.Y. and Seeburg, P.H. (1985), *DNA* 4:165–170.
Davanloo, P., et al. (1984), *Proc. Nat. Acad. Sci., U.S.A.* 81:2035–2039.
Deuschle, U., et al. (1986), *Proc. Nat. Acad. Sci., U.S.A.* 83:4134–4137.
Deuschle, U., et al. (1989), *Proc. Nat. Acad. Sci., U.S.A.* 86:5400–5404.
Dunaway, M., et al. (1980), *Proc. Nat. Acad. Sci., U.S.A.* 77:7181–7185.
Dunn, J.J., et al. (1971), *Nature New Biology* 230:94–96.
Dunn, J.J., et al. (1988), *Gene* 68:259–266.
Dunn, J.J. and Studier, F.W. (1983), *J. Mol. Biol.* 166:477–535; and erratum (1984), *J. Mol. Biol.* 175:111–112.
Fuerst, T.R., et al. (1986), *Proc. Nat. Acad. Sci., U.S.A.* 83:8122–8126.
Ghattas, I.R., et al. (1991), *Mol. Cell Biol.* 11(12):5848–5859.
Gilbert, W. and Maxam, A. (1973), *Proc. Nat. Acad. Sci., U.S.A.* 70:3581–3584.
Giordano, T.J., et al. (1989), *Gene* 84:209–219.
Golomb and Chamberlin (1974), *J. Biol. Chem.* 249:2858–2863.
Green et al. (1983), *Cell* 32:681–694.
Grodberg, J. and Dunn, J.J. (1988), *J. Bacteriol.* 170:1245–1253.
Gunderson, S.I., et al. (1987), *Biochemistry* 26:1539–1549.
Hausmann (1976), *Current Topics in Microbiology and Immunology* 75:77–109.
Hsieh, W.–T., et al. (1987), *J. Biol. Chem.* 262:14583–14591.
Ikeda, R.A., and Richardson, C.C. (1986), *Proc. Nat. Acad. Sci., U.S.A.* 83:3614–3618.
Inouye, M., et al. (1973) *J. Biol. Chem.* 248:7247–7252.
Jang, S.K. and Wimmer, E. (1990), *Genes & Development* 4:1560–1572.
Klement, J.F., et al. (1990) *J. Mol. Biol.* 215:21–29.
Korsten et al. (1975), *J. Gen. Virol.* 43:57–73.
Kotani, H., et al. (1987), *Nucl. Acids Res.* 15:2653–2664.
Kozak, M. (1989), *J. Cell Biol.* 108:229–241.
Kuhn, R., et al. (1990), *J. Virol.* [in press].
McAllister, W.T., et al. (1981), *J. Mol. Biol.* 153:527–544.
McAllister, W.T. and Carter, A.D. (1980), *Nucleic Acids Res.* 8(20):4821.
Moffatt, B.A. and Studier, F.W. (1987), *Cell* 49:221–227.
Morris, C.E., et al. (1986), *Gene* 41:193–200.

(List continued on next page.)

*Primary Examiner*—Mindy Fleisher
*Assistant Examiner*—Philip W. Carter
*Attorney, Agent, or Firm*—Margaret C. Bogosian

[57] ABSTRACT

This invention relates to the cloning and expression of autogenes encoding RNA polymerases of T7 and T7-like bacteriophages, in which the RNA polymerase gene is transcribed from a promoter which is recognized by the encoded RNA polymerase. Cloning of T7 autogenes was achieved by reducing the activity of the RNA polymerase sufficiently to permit host cell growth. T7 RNA polymerase activity was controlled by combining two independent methods: lac-repression of the recombinant lac operator-T7 promoter in the autogene and inhibition of the polymerase by T7 lysozyme. Expression systems for producing the RNA polymerases of T7 and other T7-like bacteriophages, and expression systems for producing selected gene products are described, as well as other related materials and methods.

32 Claims, 11 Drawing Sheets

OTHER PUBLICATIONS

Mossing, M.C. and Record, M.T., Jr. (1986), *Science* 233:889–892.
Nakamura, K. and Inouye, M. (1982), *EMBO J.* 1:771–775.
Oehler, S., et al. (1990), *EMBO J.* 9:973–979.
Pelletier, J. and Sonenberg, N. (1988), *Nature* 334:320–325.
Pelletier, J. and Sonenberg, N. (1989), *J. Virol.* 63:441–444.
Rodriquez, D., et al. (1990), *J. Virol.* 64(10):4851–4857.
Rose, R.E. (1988), *Nucl. Acids res.* 16:355.
Rosenberg, A.H., et al. (1987), *Gene* 56:125–135.
Schneider, T.D. and Stormo, G.D. (1989), *Nucleic Acids Res.* 17(2):659.
Schmitz, A. and Galas, D.J. (1979), *Nucl. Acids Res.* 6:111–137.
Straney, S.B. and Crothers, D.M. (1987), *Cell* 51:699–707.
Studier, F.W. (1965), *J. Mol. Biol.* 11:373–390.
Studier, F.W. and Rosenberg, A.H. (1981), *J. Mol. Biol.* 153:503–525.
Studier, F.W. and Moffatt, B.A. (1986), *J. Mol. Biol.* 189:113–130.
Studier, F.W., et al. (1990), *Methods Enzymol.* 185:60–89.
Tabor, S. and Richardson, C.C. (1985), *Proc. Nat. Acad. Sci., U.S.A.* 82:1074–1078.
Towle et al. (1975), *J. Biol. Chem.* 250:1723–1733.
Trono, D., et al. (1988), *J. Virol.* 62:2291–2299.
Wesink, P.C., et al. (1974), *Cell* 3:315–325.
Zinn et al. (1983), *Cell* 34:865–879.
Hausmann, *The Bacteriophages*, vol. I, ed., R. Calendar, Plenum Publishing Corp., 1988, pp. 259–289.
McGraw et al., *Nucleic Acids Research* 13:6753–6766 (1985).
Dietz et al., *Mol. Gen. Genet.* 221:283–286 (1990).
Masters et al., *Cell* 51:89–99 (1987).
Beck et al., *J. Mol. Biol.* 210:287–701 (1989).

| PROMOTER | SEQUENCE | | | | |
|---|---|---|---|---|---|
| | +1 | +11 | +21 | +31 | +41 |
| CLASS III | GGGAGA | | | | |
| φ10 | GGGAGA CCAC | AACGGTTTCC | CTCTAGCGGG ATCC | | |
| pET-7 | GGCCTG GATC | C | | | |
| pET-7•1 | GGGAGA GGCC | TGGATCC | | | |
| pET-7•2 | GGGGAA GGCC | TGGATCC | | | |
| pET-7•3 | GGAGAA GGCC | TGGATCC | | | |
| T7lac | GGGGAA TTGT | GAGCGGATAA | CAATTCCCCT | GGATCC | |
| T7lacL | GGGGAA TTGT | TATCCGCTCA | CAATTCCCCT | GGATCC | |
| T7lac21 | GGGAGA GGGG | AATTGTGAGC | GGATAACAAT | TCCCCTGGAT | CC |

FIGURE 1 pT7*lac*L-2a, b, c

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

TAATACGACT CACTATAGGG AGACCACAAC GGTTTCCCTC TAGCGGGATC C      51

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

TAATACGACT CACTATAGGC CTGGATCC      28

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

TAATACGACT CACTATAGGG AGAGGCCTGG ATCC      34

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

TAATACGACT CACTATAGGG GAAGGCCTGG ATCC      34

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

TAATACGACT CACTATAGGA GAAGGCCTGG ATCC  34

( 2 ) INFORMATION FOR SEQ ID NO:6:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

TAATACGACT CACTATAGGG GAATTGTGAG CGGATAACAA TTCCCCTGGA TCC  53

( 2 ) INFORMATION FOR SEQ ID NO:7:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

TAATACGACT CACTATAGGG GAATTGTTAT CCGCTCACAA TTCCCCTGGA TCC  53

( 2 ) INFORMATION FOR SEQ ID NO:8:

( i ) SEQUENCE CHARACTERISTICS:
        ( A ) LENGTH: 59 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

TAATACGACT CACTATAGGG AGAGGGAAT TGTGAGCGGA TAACAATTCC CCTGGATCC  59

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

AGATCTCGAT CCCGCGAAAT TAATACGACT CACTATAGGC CTGGATCC  48

( 2 ) INFORMATION FOR SEQ ID NO:10:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

TAATACGACT CACTATAGGG AATTGTGAGC GGATAACAAT TCC  43

( 2 ) INFORMATION FOR SEQ ID NO:11:

( i ) SEQUENCE CHARACTERISTICS:
  ( A ) LENGTH: 43 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:11:

```
TAATACGACT CACTATAGGG AATTGTTATC CGCTCACAAT TCC                    43
```

( 2 ) INFORMATION FOR SEQ ID NO:12:

( i ) SEQUENCE CHARACTERISTICS:
  ( A ) LENGTH: 42 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:12:

```
TAATACGACT CACTATAGGA ATTGTGAGCG GATAACAATT CC                     42
```

( 2 ) INFORMATION FOR SEQ ID NO:13:

( i ) SEQUENCE CHARACTERISTICS:
  ( A ) LENGTH: 43 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:13:

```
TAATACGTAC TCACTATAGG AATTGTTATC CGCTCACAAT TCC                    43
```

( 2 ) INFORMATION FOR SEQ ID NO:14:

( i ) SEQUENCE CHARACTERISTICS:
  ( A ) LENGTH: 40 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:14:

```
TAATACGACT CACTATAGAA TTGTGAGCGG ATAACAATTC                        40
```

( 2 ) INFORMATION FOR SEQ ID NO:15:

( i ) SEQUENCE CHARACTERISTICS:
  ( A ) LENGTH: 40 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:15:

```
TAATACGACT CACTATAGAA TTGTTATCCG CTCACAATTC                        40
```

( 2 ) INFORMATION FOR SEQ ID NO:16:

( i ) SEQUENCE CHARACTERISTICS:
  ( A ) LENGTH: 34 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:16:

GGGAGACCAC AACGGTTTCC CTCTAGCGGG ATCC 34

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

GGCCTGGATC C 11

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

GGGAGAGGCC TGGATCC 17

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

GGGGAAGGCC TGGATCC 17

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

GGAGAAGGCC TGGATCC 17

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

GGGGAATTGT GAGCGGATAA CAATTCCCCT GGATCC 36

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:22:

GGGGAATTGT TATCCGCTCA CAATTCCCCT GGATCC 36

(2) INFORMATION FOR SEQ ID NO:23:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:23:

GGGAGAGGGG AATTGTGAGC GGATAACAAT TCCCTGGAT CC 42

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:24:

TAATACGACT CACTATAGGG AGA 23

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

TAATACGACT CACTATAGGG GAA 23

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

GGAATTGTGA GCGGATAACA ATTCC 25

(2) INFORMATION FOR SEQ ID NO:27:

(i) SEQUENCE CHARACTERISTICS:
    (A) LENGTH: 44 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:27:

TAATACGACT CACTATAGGG GAATTGTGAG CGGATAACAA TTCC 44

(2) INFORMATION FOR SEQ ID NO:28:

(i) SEQUENCE CHARACTERISTICS:
    (A) LENGTH: 44 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:28:

TAATACGACT CACTATAGGG GAATTGTTAT CCGCTCACAA TTCC 44

(2) INFORMATION FOR SEQ ID NO:29:

(i) SEQUENCE CHARACTERISTICS:
    (A) LENGTH: 50 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:29:

TAATACGACT CACTATAGGG AGAGGGGAAT TGTGAGCGGA TAACAATTCC 50

CLONING AND EXPRESSION OF AUTOGENES ENCODING RNA POLY, ERASES OF T7-LIKE BACTERIOPHAGES

RELATED APPLICATION

This is a continuation of application Ser. No. 07/879,687, filed May 5, 1992, now abandoned, which is a continuation-in-part of application Ser. No. 07/876,972, filed May 1, 1992, now abandoned.

GOVERNMENT SUPPORT

Work described herein was supported by the Office of Health and Environmental Research of the United States Department of Energy and by Public Health Service grant GM21872 from the Institute of General Medical Services. The U.S. government has certain rights in this invention.

BACKGROUND

Bacteriophage T7 is a virulent bacteriophage that infects *Escherichia coli*. It is representative of a class of bacteriophages which specify single peptide chain RNA polymerases which specifically transcribe from cognate bacteriophage promoters and which are highly active relative to bacterial RNA polymerases. The specificity of the T7 RNA polymerase for its cognate promoters is believed to be due to the relatively large size of the promoter sequence, which makes it unlikely to occur by chance in any unrelated DNA (Chamberlin et al., 1970; Dunn and Studier, 1983). The highly conserved consensus sequence of naturally occurring T7 promoters is about 23 base-pairs (bp) and includes the RNA start site. If exact specification of even as few as 15 of these bp were required for transcription initiation, the probability of chance occurrence of a functional T7 promoter would be less than one in $10^9$ bp of DNA. T7 RNA polymerase is very efficient at transcribing from its cognate promoters, and elongates RNA chains about five times faster than *E. coli* RNA polymerase (Golomb and Chamberlin, 1974). Termination signals apparently occur infrequently and termination is usually inefficient (McAllister et al., 1981).

During infection, these properties of the T7 RNA polymerase play a part in directing all transcription and replication in the infected cell to T7 DNAs. After the bacteriophage RNA polymerase is made, other T7 gene products inactivate the host RNA polymerase, leaving all transcription in the infected cell to be catalyzed by the T7 polymerase.

The activity, ability to make complete transcripts, and specificity of T7 RNA polymerase for its cognate promoters, has led to a variety of uses. T7 RNA polymerase and SP6 (a T7-like bacteriophage) RNA polymerase have been purified from infected cells and used to synthesize RNA in vitro; the synthesized RNA has been used for in vitro translation (Dunn and Studier, 1983), as substrates for splicing (Green et al., 1983), and as hybridization probes (Zinn et al., 1983). The specific interaction of T7 RNA polymerase with its promoters can also provide a basis for expression systems in which selected genes are cloned under the control of T7 promoters. The target genes can be carried in vectors appropriate for a variety of host cells (e.g., Tabor and Richardson, 1985; Studier and Moffatt, 1986; Benton et A., 1990; Dunn et al., 1988).

T7 RNA polymerases can be produced and purified from infected cells. Natural infection, however, is a poor source of the polymerase, since the enzyme is synthesized only for a few minutes during infection and does not accumulate to high levels. In addition, natural infection as a means to transcribe genes which are placed under T7 promoters by recombinant techniques possesses further disadvantages: competition from T7 promoters in the bacteriophage DNA and lysis of the cells within a short time.

Expression of T7 RNA polymerase from the cloned gene has been recognized as a preferable source both for purified polymerase and for T7-based expression systems. Due to the high transcriptional activity of the T7 RNA polymerase, however, cloned DNA containing an active T7 RNA polymerase gene and a cognate promoter that could transcribe the gene is lethal to the cell. Indeed, cloning of an active gene for T7 RNA polymerase, and the homologous T3 and SP6 RNA polymerases, has been found to be successful only upon eliminating bacteriophage promoters which flank the coding sequence so that mRNA for the polymerase could not be made by transcribing around the plasmid (Davanloo et al., 1984; Tabor and Richardson, 1985; Morris et al., 1986; Kotani et al., 1987). Expression of T7 RNA polymerase from cloned genes has been achieved by placing the polymerase gene under an inducible promoter which is recognized by the host cell; expression systems based on these types of recombinant constructs have been described (see, in addition to the above, U.S. Pat. No. 4,952,496 by Studier et al., 1990; Fuerst et al., 1986; Rodriguez et al., 1990).

SUMMARY OF THE INVENTION

This invention relates to the cloning and expression of nucleic acid constructs, referred to herein as autogenes, which consist essentially of a gene encoding a bacteriophage RNA polymerase under the control of a promoter recognized by the encoded polymerase. The RNA polymerases encoded in these constructs are derived from a group of bacteriophages, of which T7 is the most extensively characterized. These bacteriophages, referred to herein as T7-like bacteriophages, specify single peptide polymerases which are highly active and specific for relatively large promoters. Once transcription is initiated at an autogene promoter, thereby activating the autogene, expression of the autogene proceeds in an autocatalytic manner, a process which is normally lethal to the cell.

The work described herein shows for the first time that T7-like bacteriophage autogenes have been successfully cloned and expressed in host cells. In particular, as described herein, T7 RNA polymerase autogenes have been cloned and expressed in *E. coli* cells. The establishment of T7 autogenes in bacterial host cells was achieved by controlling the basal or uninduced activity of the autogene-encoded polymerase, thus allowing the host cells to grow. Two independent methods of control were employed: lac-repression of the recombinant autogene promoter and inhibition of the RNA polymerase by T7 lysozyme. These methods of repression further permitted induction of substantial levels of T7 RNA polymerase to be produced from the autogenes.

Autogenes, expression constructs containing autogenes, and methods for producing bacteriophage RNA polymerases are included in this invention. Expression systems based on autogenes encoding the RNA polymerases of T7 and other T7-like bacteriophages and methods for producing selected gene products are further included, as well as an assay method for identifying infrequently transcribed regions of bacterial chromosomes.

BRIEF DESCRIPTION OF THE DRAWINGS

FIG. 1 shows the nucleotide sequences of different T7 promoters, from the RNA start at +1 to the BamHI cloning site. The 5' to 3' DNA sequence corresponding to the RNA initiated at the promoter is given. The BamHI site and the center of symmetry of the lac operator are underlined. The sequence given for the promoters in FIG. 1 are as follows:

| Promoter | Seq. ID # | Sequence: |
|---|---|---|
| φ10 | Seq. ID #16 | (nucleotides 18–51 of Seq. ID#1) |
| pET-7 | Seq. ID #17 | (nucleotides 18–28 of Seq. ID#2) |
| pET-7.1 | Seq. ID #18 | (nucleotides 18–34 of Seq. ID#3) |
| pET-7.2 | Seq. ID #19 | (nucleotides 18–34 of Seq. ID#4) |
| pET-7.3 | Seq. ID #20 | (nucleotides 18–34 of Seq. ID#5) |
| T7lac | Seq. ID #21 | (nucleotides 18–53 of Seq. ID#6) |
| T7lacL | Seq. ID #22 | (nucleotides 18–53 of Seq. ID#7) |
| T7lac21 | Seq. ID #23 | (nucleotides 18–59 of Seq. ID#8) |

Seq. ID #1–8 respectively show the sequences of the φ10, pET-7, pET-7.1, pET-7.2, pET-7.3, T7lacL and T7lac21 promoters from −17 to the BamHI cloning site.

Figure 2:
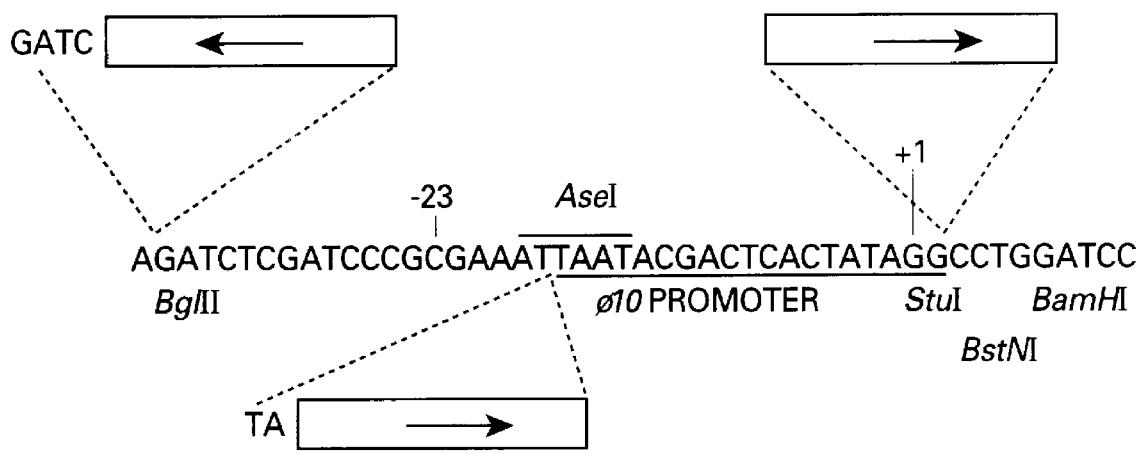

FIG. 2 shows the sites of insertion of the lac operator relative to the pET-7 promoter sequence (Seq. ID #9). The conserved class III promoter sequence from −17 to +2 is underlined and the positions of restriction sites are indicated. The boxes represent lac operator sequences and the broken lines indicate the sites of insertion. The arrows indicate the orientation of the operator sequence. Additional nucleotides generated by filling in restriction cuts in the cloning are shown. The 5' to 3' sequence of the non-template DNA strand is given.

Figure 3:
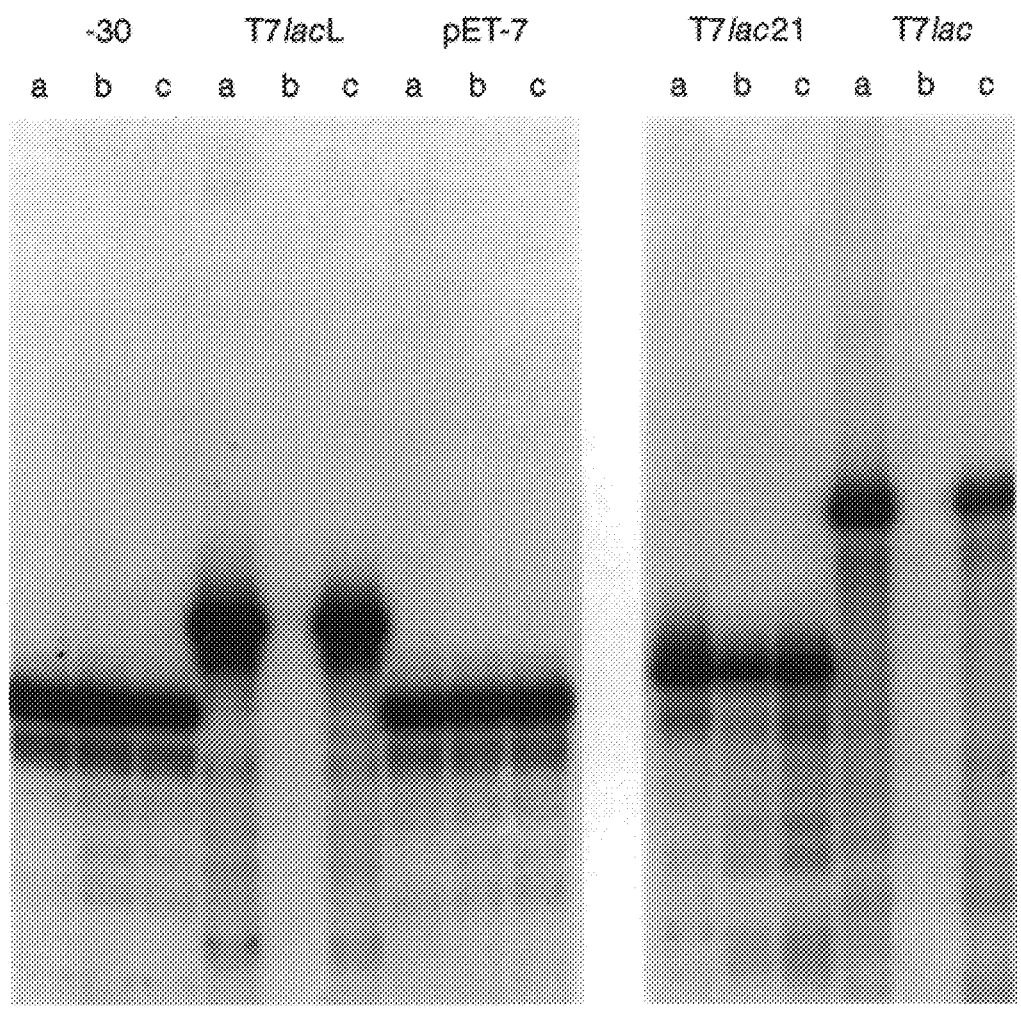

FIG. 3 shows the effect of purified lac repressor on transcription by T7 RNA polymerase from promoters having lac operators at different positions. Transcription reactions were performed in set of three, containing (a) no lac repressor; (b) 70 nM lac repressor (first three sets) or 140 mM lac repressor (last two sets); (c) lac repressor plus 1 mM IPTG. The templates were plasmid DNAs that had been linearized by cutting with a restriction enzyme. The T7 promoters were: the pET-7 promoter (operator centered at −30); the T7lacL promoter (operator centered at +15); the pET-7 promoter (no operator); the T7lac21 promoter (operator centered at +21; and the T7lac promoter (operator centered at +15). The predicted lengths of the runoff transcripts were 156, 181, 156, 187, and 223 nucleotides.

Figure 4A:
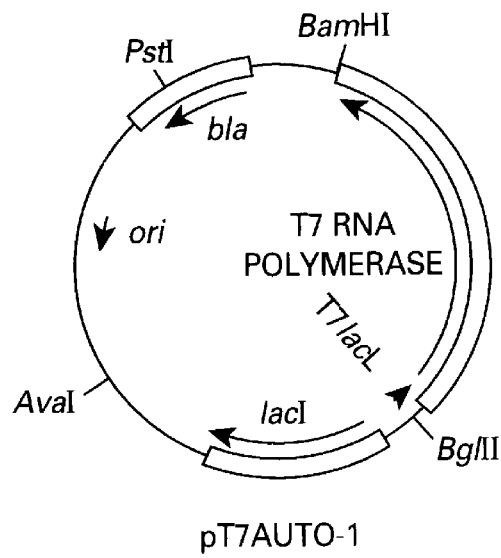
Figure 4B:
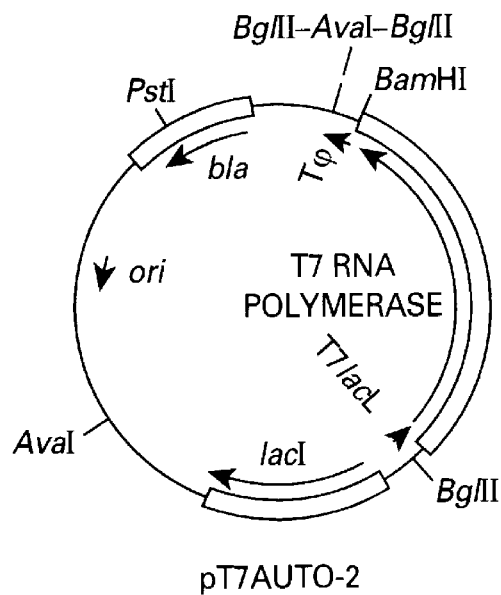

FIG. 4 is a diagram of plasmids pT7AUTO-1 and pT7AUTO-2.

Figure 5:
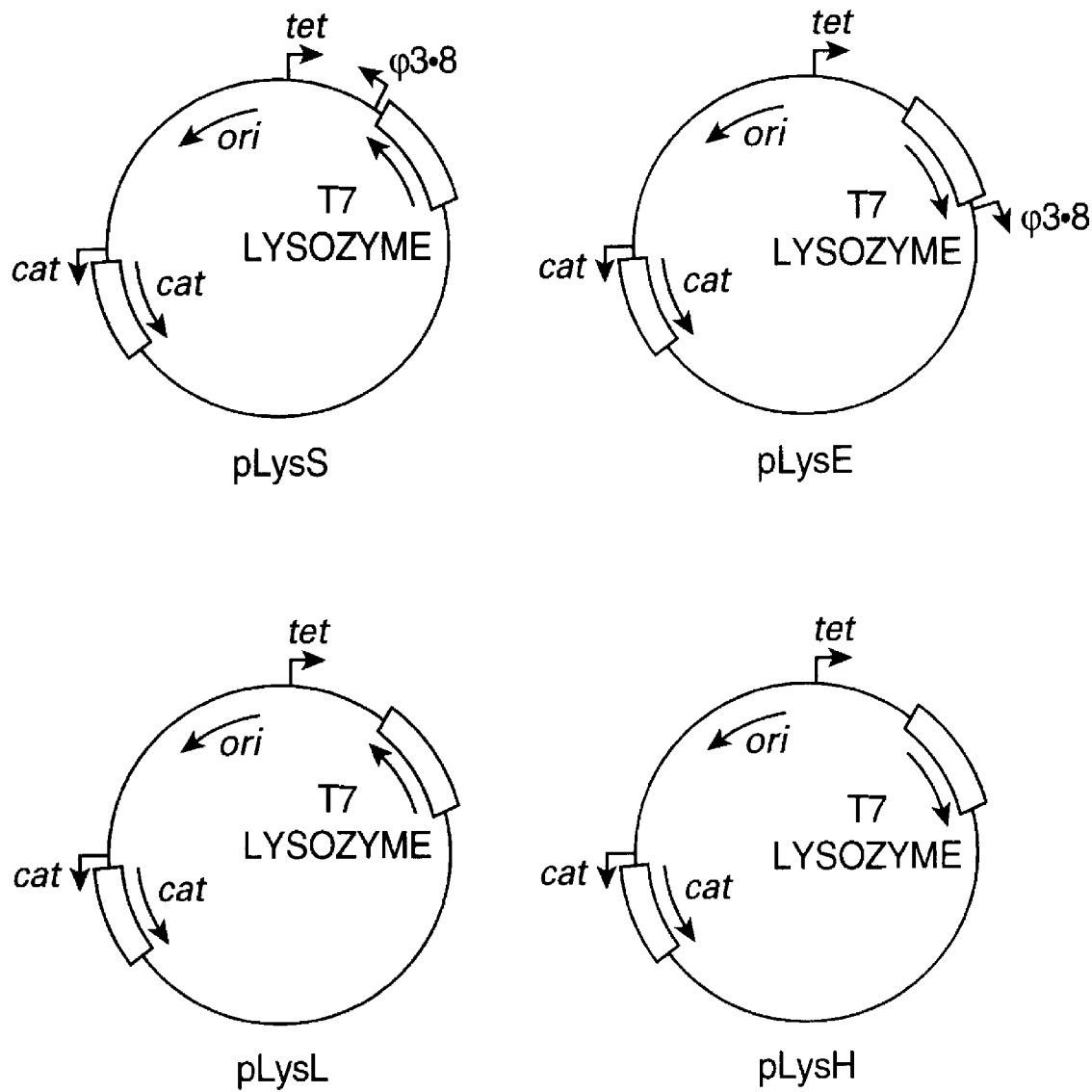

FIG. 5 is a diagram of plasmids pLysS, pLysE, pLysL, and pLysH.

Figure 6:
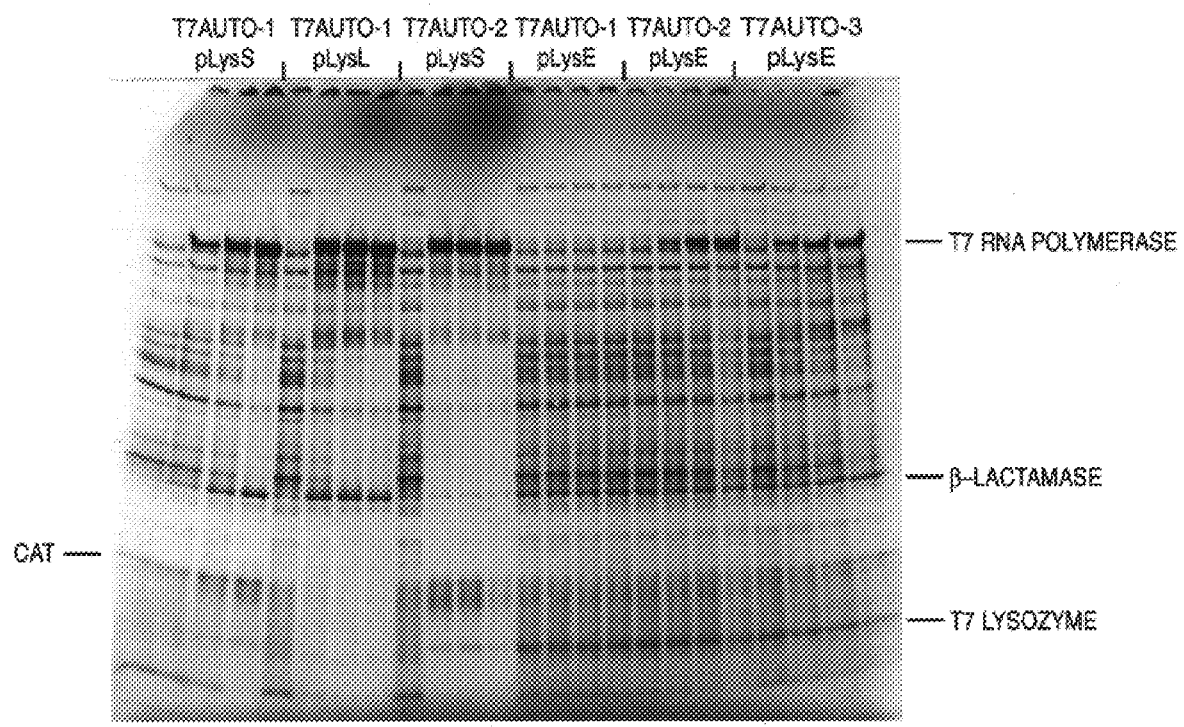

FIG. 6 shows the induction of T7 RNA polymerase from T7 autogenes in the presence of pLysL, pLysS or pLysE. Samples of cultures of HMS174 carrying the indicated plasmids were labeled with [$^{35}$S]methionine immediately before or 0.5, 1 or 2.5 hours after induction. The labeled samples were analyzed by SDS-PAGE followed by autoradiography. The positions of relevant proteins are indicated.

Figure 7:
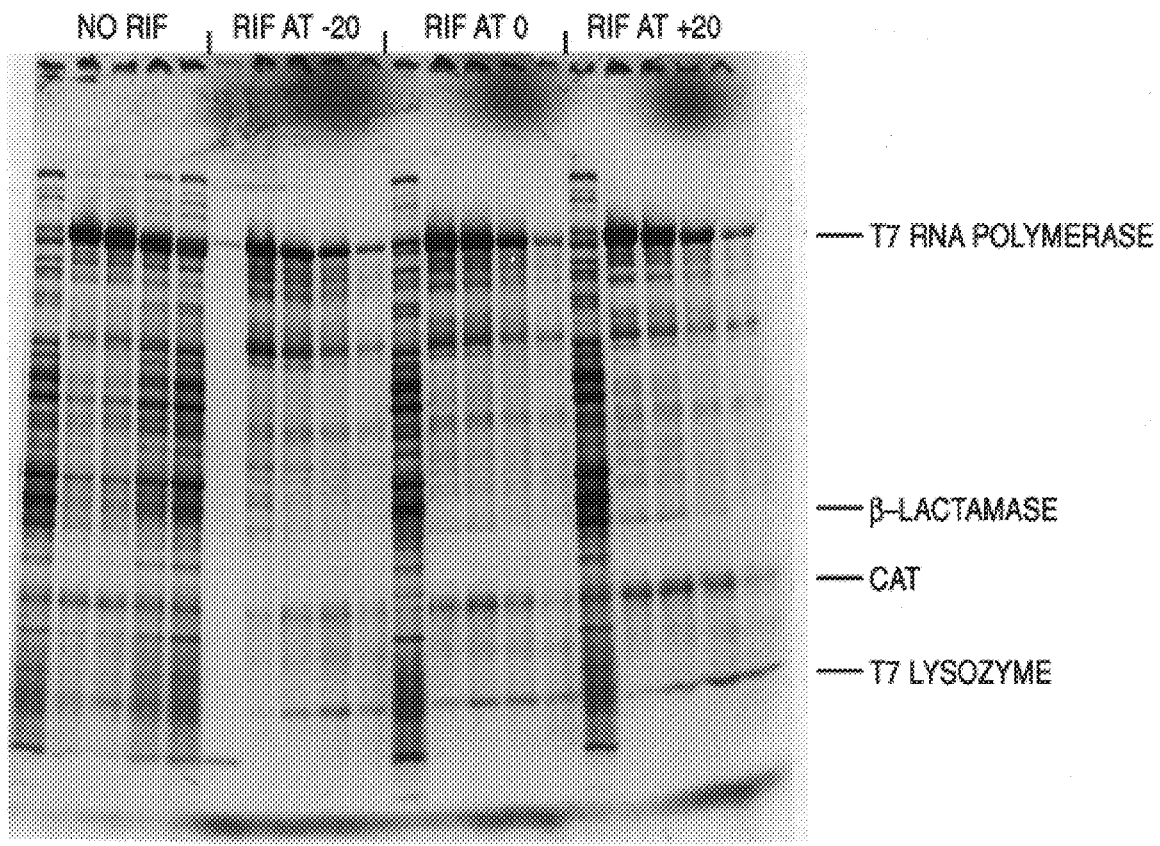

FIG. 7 shows the effect of rifampicin on induction of BL21/pLysS/pT7AUTO-2. Cultures were labeled with [$^{35}$S] methionine immediately before or 0.5, 1, 2, or 3 hours after induction in the absence or presence of 200 μg rifampicin/ml, which was added 20 minutes before induction, at the time of induction, or 20 minutes after induction, as indicated. The labeled samples were analyzed by SDS-PAGE followed by autoradiography. The positions of relevant proteins are indicated.

Figure 8:
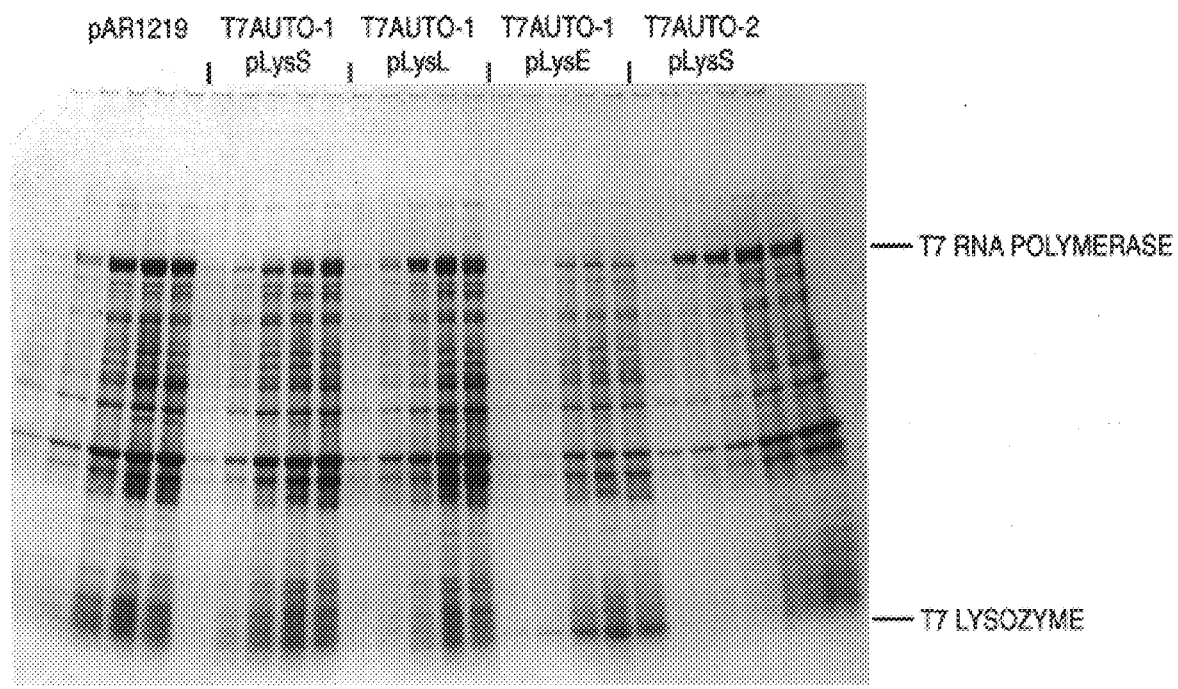

FIG. 8 shows the accumulation of T7 RNA polymerase after induction. Total protein from equivalent volumes of cultures of BL21 carrying the indicated plasmids was analyzed by SDS-PAGE followed by staining with Coomassie blue. Samples in each set were collected immediately before and at 1, 3, 6, and 17 hours after induction, except for BL21/pLysE/T7AUTO-1, where the third sample was collected at 4.5 hours rather than at 3 hours.

Figure 9:
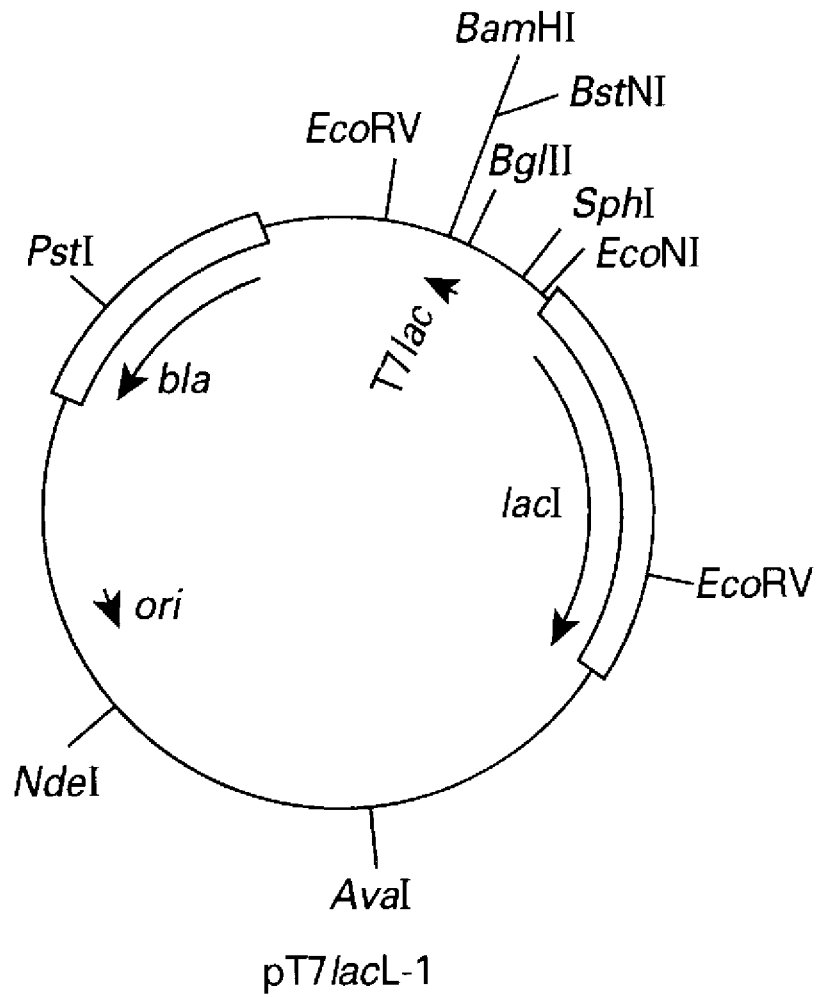

FIG. 9 is a diagram of plasmid pT7lacL-1.

Figure 10:
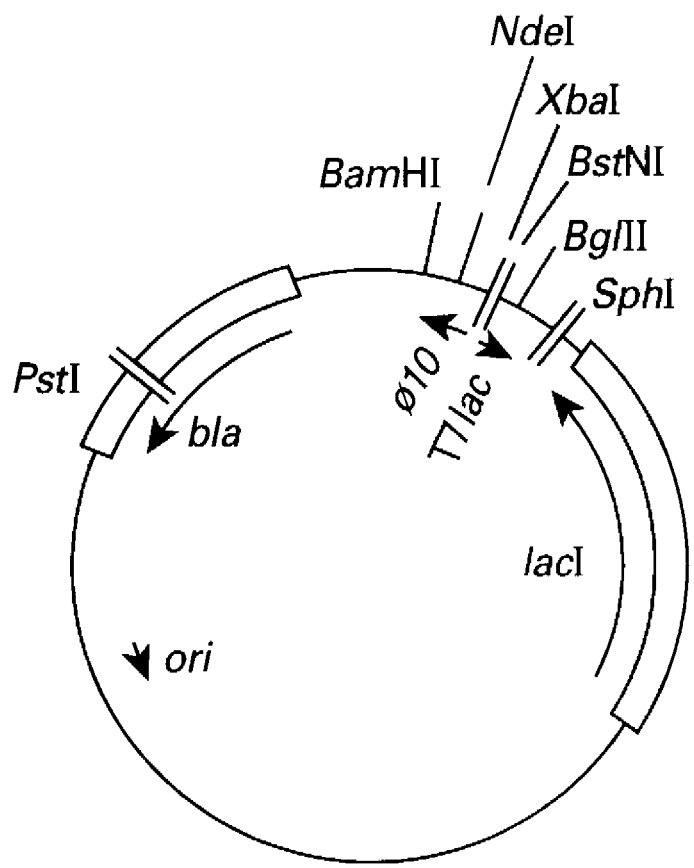

FIG. 10 is a diagram of plasmids pT7lac-2a, -b and -c.

Figure 11:
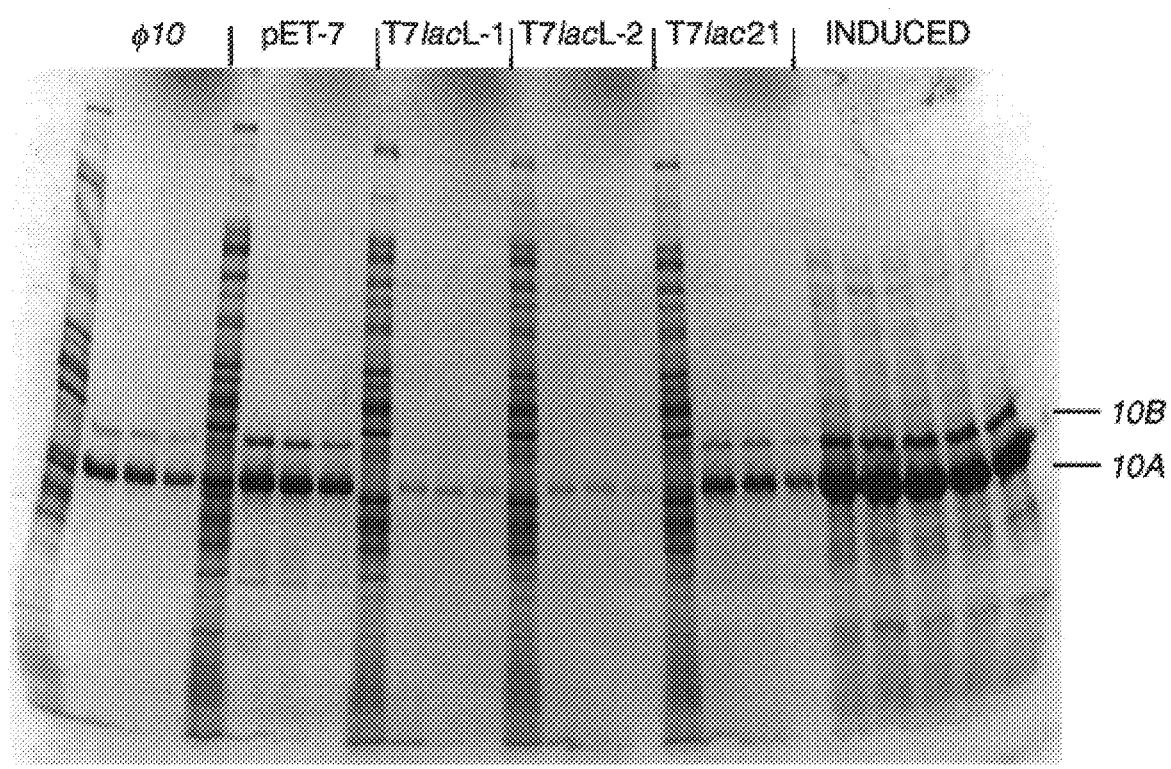

FIG. 11 shows the basal and induced expression gene 10 from different T7 promoters. Cultures of BL21(DE3) contained the gene 10 coding sequence under control of its natural φ10 promoter in plasmid pAR3625; the pET-7 promoter in plasmid pAR4367; the T7lacL promoter in pAR4348 (derived from pT7lacL-1, where the lacI promoter is directed away from gene 10); the T7lacL promoter in pAR4353 (derived from pT7lacL-2, where the lacI promoter is directed tward gene 10); or the T7lac21 promoter in pAR4442 (derived from pT7lac21-1). From left to right in each set, lanes show gel electrophoresis patterns of proteins labeled with [$^{35}$S]methionine immediately before, and 0.5, 1 and 1.5 hours after addition of rifampicin (200 μg/ml final concentration). The five lanes at the right show samples from the five cultures labeled 1.5 hours after induction in the absence of rifampicin. Positions of the major gene 10 protein, 10A, and its frameshifted relative, 10B, are indicated.

DETAILED DESCRIPTION

This invention relates to the cloning and expression of nucleic acid constructs, referred to herein as autogenes, which consist essentially of a gene encoding a bacteriophage RNA polymerase under the control of a promoter recognized by the encoded polymerase. The RNA polymerases encoded in these constructs are derived from a group of bacteriophages, of which T7 is the most extensively characterized. These bacteriophages, referred to herein as T7-like bacteriophages, specify single peptide polymerases which are highly active and specific for relatively large promoters. Once transcription is initiated at an autogene promoter, thereby activating the autogene, expression of the autogene proceeds in an autocatalytic manner.

The high transcriptional activity of activated autogenes, while potentially useful for production of substantial amounts of RNA polymerase makes cloning of the autogenes in bacterial cells extremely difficult, due to the detrimental competitive effect of autogene expression on host cell growth. The work described herein shows that T7 autogenes can be successfully cloned in bacterial host cells by reducing the basal or uninduced level of T7 polymerase activity sufficiently to allow host cell growth. Cloning of the T7 autogenes was achieved by combining two independent mechanisms for controlling T7 polymerase activity: repression of autogene transcription by interaction of lac repressor with the recombinant lac-repressible T7 promoter in the autogene and inhibition of the autogene-encoded polymerase by interaction with T7 lysozyme. As further described below, host cells containing T7 autogenes, once established, can be induced to express substantial levels of T7 RNA polymerase. Furthermore, autogenes can be cloned into vectors for production of RNA polymerase in a variety of cell types, including eukaryotic cells.

In addition to production of RNA polymerases, autogenes can be used as a source of RNA polymerase for the production of selected gene products. The gene encoding the selected product is cloned under the control of a promoter recognized by the autogene-encoded RNA polymerase, thereby making the gene a target gene for the polymerase. As described below, expression systems employing autogene-encoded RNA polymerases to transcribe target genes may be largely or completely independent of host RNA polymerases. For example, T7 expression systems are described herein which are not dependent on E. coli RNA polymerase, as is the system described in U.S. Pat. No. 4,952,496. Thus, the expression systems of the present invention can be used to produce selected gene products in a variety of host cells, including mammalian and other eukaryotic cells, as well as bacterial cells. The in vivo T7 expression systems provided by this invention combine the advantages of efficient, specific, and inducible expression of previously described T7 expression systems, with improved versatility regarding use in different cell types. For example, a host-independent source of RNA polymerase permits the expression of gene products in host cells for which promoters and transcriptional regulation are not characterized.

The following describes the cloning and expression of T7 RNA polymerase autogenes in bacterial host strains, expression plasmids containing the autogenes, and expression systems employing the autogenes, as well as methods for producing bacteriophage RNA polymerases and selected gene products in a variety of host cells. This invention is exemplified by T7 autogenes and includes autogenes based on other T7-like bacteriophages, as described below. A related use of the autogenes is also described.

Difficulties of Cloning Bacteriophage Autogenes in E. coli

Although the T7 RNA polymerase itself is not toxic to bacterial cells, T7 autogenes were found to be lethal to bacterial hosts. The natural mRNA for T7 RNA polymerase is relatively stable and efficiently translated, and T7 RNA polymerase itself is also stable and very active; therefore, a single transcript by the host RNA polymerase is potentially enough to activate the autogene. T7 polymerase is very efficient and elongates RNA chains five times faster than E. coli RNA polymerase (Golomb and Chamberlin, 1974); therefore, autocatalytic expression of the autogene may reduce the availability of metabolites, such as nucleotides and amino acids, for host cell growth and division. Since it is questionable whether any DNA can be maintained in E. coli without being transcribed at least once per generation, the basal activity of the autogene-encoded T7 polymerase needs to be controlled if the autogene is to be established and maintained in the host cell.

Two independent methods were employed to reduce the activity of T7 RNA polymerase in such a way that a T7 autogene could be established, maintained and subsequently induced. The first method was to place the gene for T7 RNA polymerase under control of a recombinant lac-repressible T7 promoter together with an adequate source of lac repressor. The second method was to coexpress T7 lysozyme with the autogene. The methods of repression were shown to have an additive effect on T7 polymerase activity; neither method of repression alone was sufficient to control the autogene. These methods of repression and factors which affect basal and induced expression levels of autogene-encoded RNA polymerase are described below.

Lac Repressible Promoters

The lac operator is a specific, twofold symmetric nucleotide sequence of about 25 base pairs (Gilbert and Maxam, 1973); Schmitz and Galas, 1979; Dunaway et al., 1980). In the absence of inducer, lac repressor binds tightly to the lac operator and can thereby interfere with initiation or elongation of transcription by E. coli RNA polymerase (Nakamura and Inouye, 1982; Deuschle et al., 1986; Straney and Crothers, 1987). In the presence of inducer, the affinity of repressor for the operator is reduced and transcription can proceed. As shown below and in other studies (Deutschle et al., 1989; Giordano et al., 1989), the lac repressor-operator interaction can also function to inhibit transcription from recombinant lac operator-T7 promoters by T7 polymerase.

Lac-repressible T7 promoters were constructed based on the nucleotide sequences of the E. coli lac operator and the consensus sequence of highly conserved naturally occurring T7 promoters (FIGS. 1 and 2; Example 1). The effect of placing lac operators at different distances from the class III promoter was examined by in vitro transcription using purified lac repressor (FIG. 3; Example 3). T7 promoters with a lac operator centered at base-pair −49, −30, +15 or +21 relative to the RNA start site were transcribed normally by purified T7 RNA polymerase in the absence of lac repressor. In the presence of purified lac repressor, transcription was strongly inhibited by a lac operator at base-pair +15, less strongly inhibited by an operator at +21, and was unaffected by an operator at either −49 or −30. Addition of the inducer IPTG relieved the inhibition of transcription. No difference in transcription behavior was detected between the two orientations of the operator at base-pair +15.

The lac repressor is thought to bind symmetrically to the operator, and footprinting experiments indicate that bound lac repressor protects about 12 to 15 bp to either side of the central nucleotide (Gilbert and Maxam, 1973; Schmitz and Galas, 1979; Dunaway et al., 1980). T7 RNA polymerase protects approximately base-pairs −20 to −4 in the absence of triphosphates and approximately −20 to +5 in the presence of GTP, which allows formation of the first two phosphodiester bonds (Ikeda and Richardson, 1986; Gunderson et al., 1987). The center of the lac repressor binding sites at base-pairs −30 and +15 are equally close to the footprint of T7 RNA polymerase bound in the presence of GTP, yet binding of lac repressor upstream from the promoter has no effect on transcription, whereas binding downstream is strongly inhibitory. Perhaps repressor and polymerase can bind without interference in both cases, but repressor bound downstream interferes with the initiation of RNA chains. Moving the binding site only 6 bp further downstream to +21 is much less inhibitory, suggesting that bound lac repressor may not be as effective in blocking elongation of RNA chains once they are initiated. Examination of the conserved sequences of T7 promoters and of the lac operator suggests that a functional operator could be centered as close as 12 bp downstream from the RNA start without interfering substantially with transcription from the unrepressed promoter.

FIGS. 1 and 2 show three lac operator-T7 promoters whose transcriptional activity is repressed by lac repressor. The T7lac and T7lacL promoters have the operator centered at base-pair +15 in different orientations,.and the T7lac21 promoter has the operator centered at base-pair +21. As shown in FIG. 2, the center of the lac operator is placed at +15 in the orientation as written (rightward) in T7lac and at +15 in the reverse orientation in T7lacL (Leftward). The T7lac21 promoter has a rightward operator centered at +21. As shown in FIG. 1, the T7lac21 promoter contains the conserved T7 class III promoter sequence: TAATACGACT-CACTATAGGGAGA Seq. ID #24 (necleotides 1–23 of Seq. ID #1), which extends from base-pairs (bp) −17 to +6 (Dunn and Studier, 1983). Nucleotides are numbered relative to the RNA start site at +1 (shown here underlined). The T7lac and T7lacL promoters contain the T7 promoter sequence: TAATACGACTCACTATAGGGAA Seq. ID #25 nucleotides 1–23 of Seq. ID #6), which differs from the naturally occurring T7 sequence Seq. ID #Seq. ID #24 nucleotidess (1–23 of Seq. ID #1) by having GA instead of AG at bp +4 and +5. All three recombinant promoters contain the lac operator fragment: GGAATTGTGAGC GGATAACAATTCC (center of symmetry underlined; Seq. ID #Seq. ID #26, nucleotides 20–44 of Seq. ID #6).

The three recombinant promoters were cloned into pBR322 vectors along with a copy of the lac repressor gene (lacI) under its own promoter and used to transform E. coli in order to test if the promoters were repressed and induced in vivo. The activity of the recombinant promoters under repressed and induced conditions was determined by a plaque forming assay and by protein synthesis of gene products (T7 major capsid protein and β-galactosidase) whose genes were inserted under the control of the promoters, as described in Example 4. The T7lac and T7 lacL promoters were found to substantially reduce basal expression of target genes (i.e., genes under the control of a T7 promoter) in the T7 expression system, with little if any effect on induced levels of expression. The two orientations of the operator centered at +15 (T7lac and T7lacL) seemed equivalent in all tests performed. In contrast, the T7lac21 promoter, in which the operator is centered 21 bp downstream from the RNA start, was significantly less repressive of uninduced expression.

The differential repression observed between the T7lac or T7lacL promoters and the T7lac21 promoter may also be affected by how closely the promoter sequence agrees with the conserved sequence of the strong class III promoters. Chain initiation at the T7lac21 promoter, which has the entire conserved sequence, may compete more efficiently against lac repressor binding than at the T7lac or T7lacL promoters, which diverge from the conserved sequence at bp +4 and +5.

T7 Autogene Expression Plasmids and Lac Repressor

Four expression plasmids containing a T7 autogene were constructed and designated pT7AUTO-1, -2, -3 and -4 (Example 6). As shown in FIG. 4, these autogene plasmids contain T7 gene 1, which encodes the T7 RNA polymerase, inserted into a pBR322 vector containing an origin of replication (ori) and a β-lactamase or ampicillin resistance gene (bla) for maintenance in bacteria. In pT7AUTO-1 and -2, the T7 polymerase gene was put under the control of the T7lacL promoter, and pT7AUTO-3 and -4 contain the T7lac21 promoter (Table 1; tables are located at the end of the Detailed Description). All four plasmids have a lacI gene with its own promoter oriented to transcribe in the opposite direction from the T7 autogene. In addition, pT7AUTO-2 and -4 contain the T7 transcriptional terminator Tφ downstream of the autogene.

The lacI gene was included on the expression plasmids because the amount of lac repressor provided by a chromosomal copy of the lacI gene is not sufficient to repress multiple copies of the lac operator on multicopy plasmids (Blackman et al., 1976). In a lac-repressed T7 expression system, both the gene for T7 polymerase in the chromosome of the host cell and the target T7lac promoter in the vector are controlled by the lac repressor, and the level of repressor must be high enough to occupy all of these operators if a low basal level of polymerase gene expression is to be achieved. As described below, sufficient lac repressor seems to be provided from a cloned copy of the lacI gene under cortrol of its own promoter in the same plasmid as the autogene.

In the autogene expression plasmids, an E. coli DNA fragment containing the natural lacd promoter and coding sequence but not the natural downstream promoter-operator sequence was inserted about 275 bp upstream from the T7 promoter. In these and similar plasmids, basal expression of a target gene, i.e., a gene under the control of a T7 promoter, is lower when the lacI promoter is directed away from the target gene; when directed toward the target gene, a small amount of transcription by E. coli polymerase apparently reads through the lacI gene into the target gene.

The plasmids pT7AUTO-2 and -4 contain, in addition to the above elements, the T7 transcription terminator Tφ downstream from the autogene. This limits most transcription by T7 polymerase to the polymerase gene. The presence of Tφ seems to increase the basal expression of target genes in these and similar plasmids.

T7 Lysozyme Inhibition

T7 lysozyme is a bifunctional protein that cuts a bond in the cell wall of E. coli (Inouye et al., 1973) and selectively inhibits T7 RNA polymerase by binding to it, a feed-back mechanism that ensures a controlled burst of transcription during T7 infection (Moffatt and Studier, 1987).

Four plasmids for expressing T7 lysozyme in bacteria were constructed: pLysS, pLysE, pLysL, and pLysH (FIG. 5; Example 2). The four plasmids contain the T7 lysozyme gene (gene 3.5) in a vector (pACYC184) which is compatible with the pBR322-based plasmids used to construct the autogenes. In pLysE (Expressed) and pLysH (High level), gene 3.5 is oriented so that the lysozyme mRNA is transcribed from the tet (tetracycline resistance) promoter in pACYC184; in pLysS (Silent) and pLysL (Low level), the gene is oriented in the opposite direction. The tet promoter is read by the E. coli RNA polymerase. The lysozyme gene (gene 3.5) in pLysE and pLysS is flanked by other T7 DNA sequences: the last 13 codons of T7 gene 3 on the 5' side and on the 3' side, the φ3.8 promoter for T7 polymerase and first 24 codon's of gene 3.8 which encodes the T7 RNA polymerase. The T7 DNA fragment in pLysS and pLysE contains bp 10,665 to 11,296 of T7 DNA. In pLysH and pLysL, the T7 DNA fragment ends at bp 11,164 and therefore, lacks the φ3.8 promoter and beginning of gene 3.8. All four plasmids contain chloramphenicol resistance markers (CAT).

Plasmids pLysS and pLysL provide a low level of T7 lysozyme to uninduced BL21(DE3) bacterial cells, and pLysE and pLysH provide a considerably higher level, as seen by levels of lysozyme in electrophoresis gels of pulse-labeled proteins from total cell extracts. The difference in lysozyme level is consistent with a higher level of expression when lysozyme mRNA can be transcribed from the tet promoter than when the gene is in the opposite orientation. The lower level of lysozyme provided by pLysS or pLysL has little effect on growth of the cell, but the higher level provided by pLysE or pLysH can reduce the growth rate or increase lag time after induction.

Plasmids pLysS and pLysE have the φ3.8 promoter for T7 RNA polymerase immediately following the lysozyme gene, whereas pLysL and pLysH lack this promoter (or any promoter for T7 RNA polymerase). Therefore, T7 RNA polymerase should be able to transcribe some lysozyme mRNA from pLysS and pLysE by reading through the plasmid from the φ3.8 promoter, but should not transcribe any lysozyme mRNA from pLysL and pLysH. The φ3.8 promoter is weak relative to the φ10 promoter used in the pET expression vectors (McAllister et al., 1981), so most transcription by T7 RNA polymerase should be directed toward the target gene when pLysS or pLysE is in the same cell with target plasmids derived from the pET vectors.

Therefore, the relative levels of lysozyme expressed from these plasmids, and consequently, the extent to which basal expression is repressed, are expected to be in the decreasing order: pLysE>pLysH >>pLysS>pLysL.

Sensitivity of Transcription from T7 Promoters to T7 Lysozyne Inhibition

Besides the amount of T7 lysozyme, another factor influencing the basal expression of autogenes is the differential sensitivity of transcription from the different autogene promoters to inhibition by this enzyme. As described in Example 5, transcription from the T7lac and T7lacL promoters was found to be significantly more sensitive to low levels of T7 lysozyme than T7lac21 or the natural φ10 promoters. These promoters, and others tested, had identical nucleotide sequences upstream from the RNA start but differed in the transcribed region. Since T7 lysozyme inhibits transcription by binding to T7 RNA polymerase, the differences in sensitivity suggest that the T7 polymerase may become insensitive during elongation, and that promoters may differ in the time it takes an initiating polymerase to reach a lysozyme-insensitive stage.

Establishment of T7 Autocenes in E. coli

The T7 polymerase autogene constructs, pT7AUTO-1 and pT7AUTO-2, could not be established in bacterial host cells (Example 6), but could be established when the host cells also contained pLysS. Furthermore, these constructs were shown to encode transcriptionally active T7 polymerase by complementation of T7 mutants which lack gene 1 (Example 7). This indicates that lac repression alone is insufficient to control autogene expression, but lac repression combined with inhibition by T7 lysozyme is sufficient.

The T7lac21 promoter is less sensitive to lysozyme inhibition than the T7lacL promoter and is less well repressed by lac repressor, as described above. Consistent with a higher basal expression from the pT7lac21 promoter, an active clone of pT7AUTO-3 could be obtained only in the presence of pLysE, the high level producer of lysozyme. pT7AUTO-3 appeared to be somewhat unstable in the presence of pLysS and could not be established in the presence of pLysL.

pT7AUTO-4, which contains the downstream Tφ terminator and is expected to have higher basal expression than pT7AUTO-3, could be established with pLysE, but the cloned cells grew poorly. This construct could not be established at all in the presence of pLysS.

Induced Levels of T7 Polymerase from Autogenes

As described above, the basal or uninduced expression of T7 autogenes in the lac-repressed, lysozyme-inhibited expression system described herein is affected by the sensitivity of the promoter to both lac repression and lysozyme inhibition, presence or absence of Tφ, and level of T7 lysozyme. As described below, induced levels of T7 RNA polymerase expressed by this system are affected by all of these factors except the sensitivity of the promoter to the lac repressor. In addition, induced levels of T7 RNA polymerase were found to be decreased through competition with the φ3.8 promoter on the lysozyme plasmids, pLysS and pLysE. Thus, particular configurations of this expression system, i.e., particular combinations of lac-repressible T7 promoter and Tφ on the autogene plasmid and T7 lysozyme plasmid, produce higher levels of T7 RNA polymerase than others and may be preferred for this reason. For example, higher levels of T7 lysozyme may result in increased stability of autogene plasmids but decreased levels of expression upon induction.

The effect of varying levels of T7 lysozyme and other factors on the production of T7 RNA polymerase from induced cells was examined. As described below, the rates of induction and accumulated levels of induced polymerase were found to be consistent with each other and with basal expression levels.

Induction of T7 Autogenes

Rates of induction of T7 RNA polymerase were determined by pulse labeling cellular proteins with [$^{35}$S]-methionine and analyzing synthesized proteins by SDS-polyacrylamide gel electrophoresis (SDS-PAGE) followed by autoradiography (FIG. 6). Cultures were labeled immediately before and at 0.5, 1 and 2.5 hours after induction.

As shown in FIG. 6, induction of T7 polymerase from pT7AUTO-1 was rapid in the presence of pLysL, a low level producer of lysozyme. Little if any label was incorporated into lysozyme after induction. Synthesis of T7 polymerase increased more slowly but still quite rapidly in the presence of pLysS, which also supplies a slightly higher level of lysozyme due to the presence of a φ3.8 promoter on the lysozyme plasmid. The φ3.8 promoter can compete with the T7lacL promoter in the autogene and can direct the synthesis of lysozyme mRNA, as shown by increased labeling of lysozyme after induction. Presumably, some combination of promoter competition and increased synthesis of lysozyme is responsible for the slower induction of the polymerase in the presence of pLysS.

In the presence of pLysE, a high level producer of lysozyme which carries the φ3.8 promoter, induction of T7 polymerase from pT7AUTO-1 was very slow. A considerable accumulation of polymerase is apparently needed to overcome the inhibitory effect of the lysozyme present at induction, and lysozyme continued to be synthesized quite actively after induction. The autogene was induced eventually, however, because only small colonies grew at low efficiency upon prolonged incubation.

In pT7AUTO-2, the autogene is followed by the transcription terminator Tφ, which limits most transcription on the autogene plasmid to the autogene itself. The effect of Tφ was to increase substantially the rate of induction of T7 polymerase. Induction of pT7AUTO-2 in the presence of pLysS was as rapid as that from pT7AUTO-1 in the presence of pLysL, in spite of competition from the φ3.8 promoter and continued synthesis of lysozyme from pLysS. In the presence of pLysE, induction from pT7AUTO-2 was much more rapid than from pT7AUTO-1, even though lysozyme continued to be synthesized at a relatively high rate in both cases.

The faster induction of T7 polymerase when the autogene is followed by Tφ could reflect a higher basal level of polymerase, more active expression of the autogene upon induction, or both. An indication that the basal polymerase activity is higher when the autogene is followed by Tφ is that pT7AUTO-1 could be established in the presence of pLysL but pT7AUTO-2 could not.

pT7AUTO-3 and -4 contain the T7lac21 promoter, which is less sensitive to both lac repression and inhibition by T7 lysozyme. In the presence of pLysE, induction of pT7AUTO-3 was considerably faster than from pT7AUTO-1, but slower than from pT7AUTO-2, which carries Tφ.

Induction of T7 Autogenes in the Presence of Rifampicin

E. coli RNA polymerase is normally sensitive to inhibition by rifampicin, whereas T7 RNA polymerase is not (Chamberlin et al., 1970). Therefore, transcription by E. coli RNA polymerase can be selectively inhibited in a sensitive host such as BL21 (but not in a resistant host such as HMS174). The effect of rifampicin on induction of BL21/pLysS/pT7AUTO-2 cultures was examined by pulse labeling and SDS-PAGE followed by autoradiography (FIG. 7). Cultures were labeled with [$^{35}$S]methionine immediately before or at 0.5, 1, 2, or 3 hours after induction in the absence or presence of 200 μg rifampicin/ml, which was added 20 minutes before induction, at the time of induction, or 20 minutes after induction.

As shown in FIG. 7, addition of rifampicin 20 minutes before addition of IPTG to a culture of BL21/pLysS/pT7AUTO-2 did not prevent substantial induction of T7 RNA polymerase, demonstrating that transcription by the basal T7 RNA polymerase is sufficient to drive induction when the T7lacL promoter is unblocked. On the other hand, the rate of synthesis attained when rifampicin was added 20 minutes before IPTG was significantly lower than when rifampicin was added with the IPTG, 20 minutes after the IPTG, or not at all, suggesting that the capacity of the cell to respond to induction may decrease with time in the presence of rifampicin.

The labeling of T7 RNA polymerase in the presence of rifampicin before IPTG was added suggests that a significant amount of transcription from the repressed T7lacL promoter by basal T7 RNA polymerase may occur in the uninduced cell. However, a small host protein was labeled to about the same extent, apparently because its mRNA survived the 20 minutes incubation in rifampicin before labeling. If the mRNA for T7 RNA polymerase is comparably stable, a considerable fraction of the labeled polymerase could have been translated from mRNA produced by host RNA polymerase before rifampicin was added, rather than reflecting the basal level of transcription by T7 RNA polymerase.

Many protein bands smaller than T7 RNA polymerase were labeled after induction in the presence of rifampicin. Since no transcript can be made by E. coli RNA polymerase, these smaller proteins must all be translated from transcripts made by T7 RNA polymerase. The T7lacL promoter ahead of the polymerase gene in pT7AUTO-2 and the φ3.8 promoter following the lysozyme gene in pLysS are the only promoters for T7 RNA polymerase known to be present in these cells. These promoters would be expected to direct the synthesis of large amounts of mRNA for T7 RNA polymerase, plus small amounts of mRNA for β-lactamase from pT7AUTO-2 and for chloramphenicol acetyl transferase (CAT) and T7 lysozyme from pLysS. However, many additional bands are apparent, most of them larger than β-lactamase. These additional bands may be due, at least in part, to internal translational starts or stops in the mRNA for T7 RNA polymerase, which should be the dominant mRNA in the induced cell.

Accumulation of T7 RNA Polymerase Induced from Autogenes

The accumulation of T7 RNA polymerase after induction was examined in cultures of BL21 carrying pT7AUTO-1/pLyS, pT7AUTO-1/pLysL, pT7AUTO-1/pLysE, pT7AUTO-2/pLysS, and pAR1219, a plasmid in which the T7 polymerase gene is controlled by the lacUV5 promoter (FIG. 8); the lacUV5 promoter is recognized by E. coli RNA polymerase. Total protein from equivalent volumes of cultures was analyzed by SDS-PAGE followed by staining with Coomassie blue. Samples for each culture were collected immediately before and at 1, 3, 6, and 17 hours after induction, except for BL21/pLysE/pT7AUTO-1, where the third sample was collected at 4.5 instead of at 3 hours.

As shown in FIG. 8, accumulations of T7 RNA polymerase upon induction of pT7AUTO-1 or pT7AUTO-2 were consistent with relative rates of induction observed by pulse labeling. Some configurations (e.g. pT7AUTO-2 in the presence of pLysS) accumulated polymerase very rapidly but none of the autogene cultures accumulated more polymerase than was obtained upon induction of pAR1219, where the polymerase gene is controlled by the lacUV5 promoter. Perhaps induction of pAR1219 produced more polymerase because induced cells carrying this plasmid could continue to grow while producing polymerase, whereas the induced autogenes ultimately stopped the growth of the cells that contained them. In at least some of the cultures, cells that had lost plasmid may have overgrown the arrested autogene-containing cells by the time the last samples were taken.

An exception was BL21/pLysE/pT7AUTO-1, where the autogene was only slightly induced: little polymerase was produced and, surprisingly, colonies developed only slightly less rapidly when these cells were plated in the presence of ampicillin and IPTG than in their absence (in contrast to HMS174/pLysE/pT7AUTO-1). Apparently, pLysE inhibits pT7AUTO-1 more strongly in BL21 than in HMS174.

As with pAR1219, essentially all of the polymerase protein produced from the autogenes was recovered in the soluble fraction of cell extracts, and the polymerase was cut by the ompT outer membrane protease when prepared from HMS174 but not BL21 (Davanloo et al., 1984; Grodberg and Dunn, 1988).

The levels of T7 RNA polymerase produced by various configurations of the expression system can be summarized as follows:

| | |
|---|---|
| High: | pT7AUTO-1 with pLysL, pT7AUTO-2 with pLysS |
| | pT7AUTO-1 with pLysS |
| to | PT7AUTO-2 with pLysE |
| | pT7AUTO-3 with pLysE |
| Low: | pT7AUTO-1 with pLysE |
| Unstable or unviable: | pT7AUTO-2 with pLysL |
| | pT7AUTO-3 with pLysL |
| | PT7AUTO-3 with pLysS |
| | pT7AUTO-4 with pLysL, -S, or -E |

In addition, stable bacterial clones containing pT7AUTO-1 and pLysH were obtained, suggesting that either pT7AUTO-1 or pT7AUTO-2 in combination with pLysH can also be used to produce T7 RNA polymerase.

Other Embodiments of Autogenes and Autogene Promoters

Autogenes for expressing the RNA polymerases of other T7-like bacteriophages can be constructed following the T7 autogene model. Other bacteriophages have been described which have single peptide chain RNA polymerases and which are specific for relatively large promoters, including E. coli phages T3, φI, φII, W31, H, Y, A1122, cro, c21, c22, and c23, the Pseudomonas putida phage gh-1, the Salmonella typhimurium phage SP6, the Serratia marcescens phage IV, the Citrobacter phage ViIII, and the Klebsiella phage K-11 (Hausmann, 1976; Korsten et al., 1975; Dunn et al., 1971; Towie et al., 1975; Butler and Chamberlin, 1982). The promoter specificities of some of these polymerases have been determined and in some cases, partially overlap. Autogenes encoding RNA polymerases with non-overlapping promoter specificities may be used to control different sets of genes independently in a single cell. RNA polymerases of some T7 bacteriophages may have especially useful properties such as optimum ranges of temperature, pH, or ionic strength, kinetics, or stability. T7-like bacteriophages occur widely in nature and infect a variety of bacteria; novel bacteriophages can be isolated which may possess RNA polymerases with unusual properties.

The genomes of all of the T7-like bacteriophages examined have been found to have a similar organization to that of T7. The RNA polymerase genes and promoters of bacteriophages T3 and Sp6 have been described (e.g., Kotani et al., 1987; Morris et al., 1986). RNA polymerase genes and promoters of other T7-like bacteriophages, including novel bacteriophages, can be identified and isolated by the methods used for T7, as described in U.S. Pat. No. 4,952,496, "Cloning and Expression of the Gene For Bacteriophage T7 RNA Polymerase" by Studier et al. (published Aug. 28, 1990) and Dunn and Studier (1983), which are hereby incorporated by reference.

The three lac-repressible promoters, T7lac, T7lacL, and T7lac21, exemplify some of the variations which are possible in autogene promoters. Autogene promoters may contain a naturally occurring bacteriophage promoter or the nucleotide sequence of a naturally occurring promoter which has been altered. Alterations in promoter sequence can produce functional promoters which are still transcribed by the autogene-encoded polymerase but which have different promoter strengths (stronger or weaker) from the natural promoter. Alterations in bacteriophage promoter sequences which produce useful autogene promoters may be determined by testing the variant promoters for transcription in vitro or in vivo, as described herein (Examples 3 and 4). Variant bacteriophage promoters may be obtained by site-directed mutagenesis or synthesized; methods of mutagenizing bacteriophage promoters and testing mutagenized promoters have been described (e.g., Klement et al., 1990; Chapman and Wells, 1982; Chapman and Burgess, 1987; Schneider and Stormo, 1989).

Alterations of bacteriophage promoters may be made based on knowledge about the nucleotide sequences and relative strengths of naturally occurring promoters. For example, natural T7 promoters have been classified in three groups (Dunn and Studier, 1983; McAllister and Carter, 1980). Class III promoters have a completely conserved sequence from −17 to +6 relative to the transcriptional start site; these promoters seem to be the strongest T7 promoters in vitro and in vivo. Class II promoters seem to be weaker than the class III promoters, and differ from the conserved class III promoter sequence at from two to seven positions. Most of the differences occur in positions +3 to +6; bases −17 to +2 appear to be somewhat conserved. Thus, stronger T7 autogene promoters can be constructed which contain the conserved class III sequence and weaker autogene promoters can be constructed which contain naturally occurring class II promoters or class III promoter sequences which have been altered. The T7lac21 promoter containing the conserved class III sequence (TAATACGACTCACTATA GGGAGA; nucleotide at +1 underlined; Seq. ID #24 nucleotides 1–23 of Seq. ID #1) and the T7lac promoter containing the variant sequence (TAATACGACTCACTATA GGGGAA; Seq. ID #25, nucleotides 1–23 of Seq. ID #6) are examples; the T7lac21 promoter is stronger and less well repressed by lac repressor than the T7lac promoter.

As described above, regulatable autogene promoters can also be constructed; regulatable promoters are useful for controlling the activity of the autogene-encoded polymerase when establishing the autogene in host cells, as well as providing for inducible expression of the autogene-encoded polymerase. A regulatable autogene promoter consists essentially of a promoter element and a regulatory element. The promoter element is a promoter which is recognized by the autogene-encoded RNA polymerase and can be a natural bacteriophage promoter or a variant of a natural bacteriophage promoter sequence, as described above. The regulatory element can be the binding site of any DNA-binding protein which binds to a specific nucleotide sequence. The DNA-binding protein can be a transcription factor, repressor, replication factor, or other protein whose specific binding site is known. The binding site is placed at a distance and location from the promoter element such that binding of the DNA-binding protein interferes with transcription from the autogene promoter. The function of various configurations of promoter element and binding site may be determined by constructing the various autogene promoters and testing the promoters in vitro or in vivo, as described herein and in other studies. Data about the interaction of a DNA-binding protein with its binding site, for example, from footprinting analysis, can be also be used to predict configurations of promoter element and DNA-binding site which will result in regulation of the autogene promoter. Different placements of a DNA-binding site relative to the promoter element may produce autogene promoters having different degrees of promoter strength. In addition, the orientation of the binding site of some DNA-binding proteins may affect promoter activity.

Lac-repressible T7 autogene promoters (T7lac and T7lacL) have been described above, in which the lac operator (Seq. ID #26; nucleotides 20–44 of Seq. ID #6) is centered at +15 relative to a T7 promoter in either orientation (FIGS. 1 and 2). As mentioned above, other lac-repressible T7 promoters may be constructed in which the lac operator is centered at a position from +12 to +21 and present in either orientation relative to the transcriptional start site as in Seq. ID #10–15.

Autogenes, autogene constructs and lysozyme constructs, may be constructed using recombinant DNA techniques, including the methods described herein and other techniques, such as polymerase chain reaction. T7 DNA may be obtained from cloned DNA or chemically or enzymatically synthesized. These and other recombinant DNA techniques have been described (see, e.g., Ausubel et al.).

Expression Systems for Production of T7-like Bacteriophage RNA Polymerases

The expression system described herein, comprising lac-repressible T7 autogene plasmids and T7 lysozyme plasmids, has been shown to be useful for producing T7 RNA polymerase in bacterial cells. In this system, a combination of lac-repression and inhibition by T7 lysozyme reduces the activity of the T7 RNA polymerases sufficiently to permit growth of bacterial clones containing the autogene. The lac-repressor and T7 lysozyme are provided by the lacI and T7 lysozyme genes cloned on multicopy plasmids; these genes are under the control of promoters which are transcribed by the host RNA polymerase. For expressing autogenes encoding the RNA polymerases of other bacteriophages, cognate bacteriophage lysozyme genes should be used. The lysozyme genes of other bacteriophages may be identified and isolated by methods used for T7 lysozyme, as described in Moffatt and Studier (1987).

Other methods of reducing autogene-encoded RNA polymerase activity may be employed besides inhibition by lysozyme and lac-repression. For example, the translational efficiency of the autogene transcript may be reduced by deletion or alteration of the conserved prokaryotic ribosome binding site (Shine-Dalgarno sequence) in the autogene. The copy number of the autogene may be reduced in the cell by placing it in the host chromosome or on a low copy number plasmid; for example, autogenes may be cloned in yeast vectors containing a centromere for maintenance in yeast host cells. A drastic reduction in copy number, in translation of the polymerase, or both would be expected to result in a substantial decrease in the levels of autogene-encoded polymerase and may permit autogenes to be established in the absence of lac-repression and/or lysozyme inhibition.

Autogene-encoded bacteriophage RNA polymerases may potentially be expressed in a variety of host cell types: in prokaryotic, eukaryotic, and archaebacterial cells; in microbial, plant, insect, and animal cultures. Cloning vectors containing origins of replication and selectable markers appropriate for maintenance, promoters for expression of foreign genes in a variety of host cells, and methods for introducing constructs into host cells are described in many scientific publications or are commercially available. The autogenes, lacI genes, and lysozyme genes can be cloned into vectors appropriate for the particular host cell. The lacI and lysozyme genes may be cloned under the control of a host RNA polymerase. Alternatively, as discussed above, the autogene may be maintained in a host cell without lac-repression and lysozyme inhibition by integration of a single copy of the autogene in the host chromosome, engineering the autogene sequence to express an inefficiently translated transcript, or a combination of both.

In a further embodiment of autogene-based expression systems, the autogene may be introduced into the host cell for a single, uncontrolled burst of expression of the autogene-encoded RNA polymerase rather than maintaining an autogene in the host cell from which expression of the RNA polymerase can be induced. The RNA polymerase produced in this manner is more useful for transient expression of target genes than for production of purified bacteriophage RNA polymerases, and will be described further below.

A Further Advantage of Expression Systems Containing T7 Lysozyme

A further advantage of expression systems containing T7 lysozyme is that the presence of T7 lysozyme facilitates purification of target proteins from the host cells. T7 lysozyme cuts a bond in the cell wall of $E.$ $coli$ (Inouye et al., 1973) besides inhibiting T7 RNA polymerase. Nevertheless, cells are able to tolerate substantial levels of lysozyme, apparently because the enzyme is unable to penetrate the cell membrane to reach its substrate in the peptidoglycan layer. Treatments that disrupt membranes cause lysis of cells that contain even very small amounts of T7 lyozyme (Moffatt and Studier, 1987).

The presence of any of the T7 lysozyme plasmids can facilitate the preparation of cell extracts for purification of target proteins. Simply collecting the cells by centrifugation and suspending them in 50 mM Tris-HCl, 2 mM $Na_3EDTA$ (pH 8.0) makes them highly susceptible to lysis by agents that disrupt cell membranes. Thorough lysates of such cell suspensions can be made by freezing and thawing or by adding agents such as 0.1% (v/v) Triton X-100, 0.2% (w/v) deoxycholate or 1% (v/v) chloroform.

Expression of Selected Gene Products

In addition to production of RNA polymerases, autogenes can be used as a source of RNA polymerase for expressing selected gene products. Genes encoding the selected products can be cloned under the control of cognate promoters, thereby making them target genes for transcription by the autogene-encoded RNA polymerase. Inducible T7 expression systems can be constructed by combining the lac-repressed autogene and T7 lysozyme plasmids described above with expression vectors containing a T7 promoter for high level expression of selected gene products in $E.$ $coli$. Furthermore, as described above, inducible expression systems based on T7 and other T7-like bacteriophage RNA polymerases can be adapted to a variety of host cell types. As mentioned previously, the presence of T7 lysozyme in the expression system will facilitate the purification of target gene products from $E.$ $coli$ host cells. In addition, the availability of combinations of autogene and lysozyme plasmids which express different levels of T7 RNA polymerase provide means for controlling the level of target gene product expressed by this system.

The expression system described above requires host RNA polymerase for expression of the lac repressor and T7 lysozyme. Other expression systems for producing selected gene products are provided by this invention which largely or completely bypass the need for host RNA polymerase. These host-independent expression systems permit expression of selected gene products in a wide variety of host cell types, including cell types for which promoters and transcriptional regulatory elements have not been characterized. Furthermore, the autogene and target gene can be cloned in shuttle vectors for expression in more than one host cell type, for example, in both bacterial and mammalian cells.

As described above, autogenes may be established without control by lac repressor or T7 lysozyme; autogenes may be established in host cells by reducing autogene copy number, translational efficiency, or both. Furthermore, expression of autogenes and target genes may be obtained without regard for long term maintenance of the constructs in the host cells; the autogenes and target genes may be introduced into host cells for uncontrolled, transient expression of the target gene product.

As described above, a low level of basal expression of autogenes occurs in bacterial host cells even under tight control by lac repressor and T7 lysozyme. Since the only RNA polymerase which transcribes the autogene promoter is encoded by the autogene itself, it appears that some transcription of the autogene occurs by the host RNA polymerase; the host RNA polymerase may read across the autogene from some other place in the plasmid which contains the autogene. The induction of autogene-encoded polymerase following incubation in rifampicin, as described above, indicates that the small amount of active polymerase produced by basal expression of the autogene is sufficient to activate the autogene and start autocatalytic expression once the promoter is released from lac-repression.

In other host cells besides bacterial cells, activation of the autogene may also occur as a result of low level basal expression of the autogene. If necessary, the small amount of RNA polymerase needed to activate the autogene may be delivered into the host cell in the form of active enzyme, or mRNA or DNA encoding the active polymerase. Active polymerase, mRNA and DNA may be delivered by liposomes; the nucleic acid may also be delivered by viral infection or a variety of transfection procedures, including $CaPo_4$ precipitation, electroporation, cell fusion, or receptor-mediated uptake.

Another factor that may need to be considered in constructing autogenes and target genes for expression in eukaryotic cells is the translational efficiency of the polymerase and target gene mRNAs. Two features of eukaryotic mRNAs seem to be important for efficient translation (Kozak, 1989). Eukaryotic mRNAs have a 5' "cap" consisting of a methylated guanylate residue linked to the 5' end of the transcript by a 5'—5' pyrophosphate linkage; uncapped mRNAs are translated poorly in eukaryotic cells. The sequence surrounding the initiation codon also appears to be important for ribosome recognition; the consensus sequence of this eukaryotic translation signal, also referred to as the Kozak sequence, is 5'-ACCAUGG-3', where the initiation codon is shown underlined. In the scanning model of translation initiation proposed by Kozak, the ribosome complex recognizes first the capped 5' end of the mRNA and scans for the Kozak sequence around the initiation codon; translation then begins at the first AUG in the mRNA.

Recently, an alternative eukaryotic ribosome recognition mechanism has been described which does not require 5' caps. The mRNAs of Picorna viruses, a family of plus-strand RNA viruses, have been found to be translated from an internal site in the long 5' untranslated regions of the mRNAs. The internal site, referred to as an internal ribosomal entry site (IRES), has been proposed to be an attachment site for eukaryotic ribosomes. The IRES of encephalomyocarditis (EMCV) mRNA has been characterized (Jang and Simmer, 1990) and similar elements have been identified in poliovirus RNA (Pelletier and Sonenberg, 1988, 1989;

Trono et al., 1988) and aphthovirus RNA (Kuhn et al., 1990). Incorporation of an IRES into autogene and target gene constructs is a preferred method of increasing translational efficiency in eukaryotic host cells, since the IRES permits cap-independent translation. In addition, IRES can be used to translate polycistronic mRNAs in eukaryotes, as described in Ghattas et al. (1991), which is hereby incorporated by reference. Thus, autogenes and target genes containing an IRES, such as that of ECMV mRNA, in the 5' untranslated region of each gene and the eukaryotic Kozak sequence around each initiation codon are expected to be translated efficiently in eukaryotic host cells.

For transient expression, target genes and autogenes may be introduced directly into the cytoplasm by delivery methods which include, but are not limited to, viral infection, $CaPO_4$ precipitation, liposomes, electroporation, cell fusion, or receptor-mediated uptake.

The relative promoter strengths and translational efficiencies of the autogene and target gene may be adjusted to optimize the system for expression of the target gene product; stronger expression of the target gene product relative to the autogene-encoded RNA polymerase, or vice versa, may yield higher accumulated levels of the target gene product. Autogene and target gene promoters of various strengths may be obtained by alteration of the bacteriophage promoter sequence, as described above. Varying degrees of translational efficiency may be obtained by alteration of the Kozak consensus sequence or IRES sequence. The optimum configuration of autogene and target gene promoter sequences and translation signals for producing the target gene product may be determined empirically using the methods of mutagenesis and in vivo and in vitro expression assays described herein and in other studies.

Assay for Infrequently Transcribed Chromosomal Regions

The ability to tolerate a bacteriophage RNA polymerase autogene may be a sensitive way to test for bacterial chromosomal sites that are transcribed only very infrequently by the host RNA polymerase. Random integration of the autogene in different sites in the bacterial chromosome should result in differential expression of the autogene depending on the flanking host sequences. The 5' sequence of a transcript produced by T7 polymerase will be the same whatever the context of the autogene, but the 5' sequence produced by E. coli RNA polymerase will depend on the DNA sequence that surrounds the autogene. Differences in flanking sequence, by affecting the stability or efficiency of translation of the autogene mRNA, may affect the basal level of T7 RNA polymerase and therefore, the ability to tolerate the autogene at different sites. Levels of host transcription lower than that across the BamHI site of pBR322 or absence of transcription at a particular integration site may permit the autogene to be tolerated in the absence of T7 lysozyme or lac repressor. Chromosomal regions which are actively transcribed may result in lethality, and thus, provide a means for selecting those clones which can tolerate the autogene.

The autogene can be randomly integrated into the host chromosome by a variety of known methods, including transduction and transposition. Alternatively, the transcriptional activity of a particular chromosomal site can be examined by site-specific integration through homologous recombination. Clones which tolerate the autogenes would presumably have the autogenes integrated in a chromosomal region which has low transcriptional activity or which is inactive; these clones would be selected for by their ability to grow. The site of integration of the autogene in the clones can be identified by various methods, including Southern blot analysis with a nucleic acid probe containing an autogene-specific sequence, genomic sequencing using a primer containing an autogene-specific sequence, and restriction mapping. Furthermore, the infrequently transcribed region of chromosomal DNA can be isolated by cloning, by polymerase chain reaction using a primer containing an autogene-specific sequence, and other techniques.

The following examples illustrate the invention, and are not intended to be limiting in any way.

MATERIALS AND METHODS

The following materials and methods were used in the Examples.

Bacterial strains

E. coli strains HMS174 (F$^-$hsdR recA Rif$^R$) and BL21 (F$^-$hsdS gal) (Studier and Moffatt, 1986) were used as hosts for plasmids. HMS174 is $r_K^- m_K^+$ and BL21 is $r_B^- m_B^-$. The lysogens BL21(DE3) and HMS174(DE3), which contain a single chromosomal copy of the gene for T7 RNA polymerase under control of the lacUV5 promoter, were used for expressing genes under control of a T7 promoter (Studier and Moffatt, 1986). BL26 is a lac deletion derivative of BL21 obtained by P1 transduction of the U169 argF-lac deletion from LE392.23 (obtained from National Cancer Institute, Frederick, Md.); BL26(DE3) is the corresponding lysogen that provides T7 RNA polymerase.

T7 DNA and Bacterial Plasmids

The nucleotide sequence and locations of T7 genes and genetic elements in T7 DNA have been described (Dunn and Studier, 1983). Plasmid clones of T7 DNA were derived from pBR322 and provide resistance to ampicillin (Studier and Rosenberg, 1981; Bolivar et al., 1977). T7 DNA sequences are carried in the BamHI site, oriented so that the left-to-right direction in T7 DNA goes counterclockwise in pBR322. Since all of the plasmids have basically the same arrangement, elements from different plasmids were easily combined to form new plasmids by ligation of appropriate PstI-BamHI or PstI-BglII fragments.

Plasmids pAR1173 and pAR1219 (Davanloo et al., 1984) have an active gene for T7 RNA polymerase (T7 gene 1) cloned as a BamHI fragment. A unique BglII site just inside the upstream BamHI site of pAR1173 is useful for placing the gene under control of different promoters. The polymerase gene in pAR1219 is controlled by the inducible lacUV5 promoter.

The source of the T7 transcription terminator Tφ was pET-3, which has a unique BamHI site upstream from Tφ (Rosenberg et al., 1987).

The pET plasmid vectors for expressing genes under control of T7 transcription and translation signals are described by Rosenberg et al. (1987) and Studier et al. (1990); they are derived from pBR322. The suffixes "a", "b" and "c" in the pET designation identify the reading frame of the BamHI cloning site relative to the translation start, and the suffix "d" indicates that the initiation codon is part of the NcoI site rather than the NdeI site.

The compatible plasmid pLacS, which supplies lac repressor, is derived from pACYC184 (Chang and Cohen, 1978). Plasmid pLacS carries the lacI gene and its natural promoter in the BamHI site of pACYC184, oriented so that the lac promoter opposes the tet promoter: the lacI fragment contains base-pairs −50 to +1152 relative to the RNA start of the lacI promoter and extends 40 bp past the lac termination codon; it was obtained as a HincII-BanI fragment from pMC1 (Calos, 1978) cloned initially in the BamHI site of pBR322 by means of BamHI linkers (plasmid pAR3712).

Isolation of Plasmid DNA

The following rapid and convenient procedure was used to prepare plasmid DNA from 1 ml of culture. It is based on elements of the alkaline extraction procedure of Birnboim and Doly (1979), an old observation that linear DNA is efficiently precipitated in alkaline magnesium salts (Studier, 1965), and the well-known rapid lysis of cells by boiling in 1% (w/v) sodium dodecyl sulfate. The resulting plasmid DNA is suitable for transformation and restriction analysis, and has been used for sequencing.

Samples are processed in 1.5 ml polypropylene tubes and centrifugation is at room temperature in an Eppendorf-type centrifuge. The 1 ml of culture, usually grown by standing overnight at 37° C. in M9ZB (Studier and Moffatt, 1986) plus appropriate antibiotic, is centrifuged for 30 seconds, the supernatant removed by aspiration, and the pellet suspended in 100 µl of water. To this suspension is added 100 µl of 0.1M NaOH, 10 mM EDTA, 2% sodium dodecyl sulfate, which is mixed immediately by vortexing because the samples rapidly become viscous. The tube is heated for 2 minutes in a boiling waterbath, 50 µl of 1M MgCl$_2$ is mixed in by vortexing, and the tube is placed on ice for 2 minutes. The precipitate is pelleted by centrifuging for 30 seconds, 50 µl of 5M potassium acetate is mixed into the supernatant in the same tube by brief vortexing, and the tube is again placed on ice for 2 minutes. After centrifuging another 30 seconds, the supernatant is removed to a new tube containing 0.6 ml of 95% (v/v) ethanol, mixed by vortexing and placed on ice for 2 minutes. The tube is centrifuged for 1 minute, the supernatant is removed by aspiration, and 0.5 ml of 70% ethanol is added, vortexed, centrifuged for 1 minute and removed by aspiration. Residual solvent is removed under vacuum for 5 to 10 minutes and the pellet dissolved in a convenient volume of the desired solvent, typically 50 µl of 10 mM Tris, 0.1 mM EDTA (pH 8.0).

The basic procedure can take less than 30 minutes but samples can be left longer on ice at any stage, or even at room temperature instead of on ice, which can be convenient when preparing many samples. The resulting plasmid DNA should be essentially free of chromosomal DNA but will contain RNA fragments, which can be removed by treatment with RNase.

Plasmid Transformations

Plasmids were introduced into cells by treatment with calcium chloride as described by Wensink et al. (1974). When testing for ability to establish target plasmids (i.e., plasmids containing T7 promoters), transformability of the cells was verified with a plasmid known to be tolerated, and transforming capacity of the plasmid preparation was verified on isogenic cells that lacked the gene to T7 RNA polymerase, all in the same experiment.

Induction of Bacterial Cultures

Plasmids containing genes cloned under control of a T7 promoter were expressed in BL21(DE3) or BL26(DE3) growing in M9 medium at 37° C., essentially as described (Studier and Moffatt, 1986; Studier et al., 1990). Typically, a culture was grown overnight at 30° C. from a dilution of $10^4$ or greater in ZB that contained 20 µg ampicillin/ml to select for the target plasmid and 25 µg chloramphenicol/ml to select for pLysS or pLacS, if present. This culture, which typically had barely grown to saturation, was diluted by a factor of $10^4$ in M9 medium plus appropriate antibiotics, grown overnight at 30° C., and shifted to 37° C. the next morning. Expression was induced by the addition of 0.4 mM isopropyl-β-D-thiogalactopyranoside (IPTG) when the $A_{600}$ of the culture reached 0.4 to 0.6. Rifampicin, which inhibits host but not T7 RNA polymerase, was used in some experiments at a concentration of 200 µg/ml.

To label proteins, 50 µl samples of culture were added to 2 µl of water containing 1 µCi of [$^{35}$S]methionine at 37° C. for 3 minutes. Total cell proteins were analyzed by electrophoresis in polyacrylamide gradient gels in the presence of sodium dodecyl sulfate, essentially as described (Studier et al., 1990).

EXAMPLE 1

Construction of Lac-Repressible T7 Promoters

The completely conserved T7 class III promoter sequence (TAATACGACTCACTATAGGGAGA; Seq. ID #24, nucleotides 1–23 of Seq. ID #1) extends from base-pair −17 to +6, relative to the start site of the RNA (Dunn and Studier, 1983). The T7 promoters used here all match the class III φ10 promoter sequence from base-pair −23 through at least +2, and all are followed at some point by a unique BamHI site that can be used to join them to other DNAs (FIGS. 1 and 2). The promoter in plasmid pET-7 matches the conserved class III promoter sequence through base-pair +2, where a StuI cleavage site allows insertion of DNA (Rosenberg et al., 1987). The pET-7.1, pET-7.2 and pET-7.3 promoters were made by inserting the appropriate synthetic DNA duplex between the StuI and BamHI sites of the pET-7 promoter, recreating a unique StuI cleavage site after base-pair +8. The pET-7.1 promoter matches the conserved class III sequence through base-pair +6; plasmids pET-7.2 and pET-7.3 are identical to pET-7.1, except in base-pairs +3 through +5 of the conserved promoter sequence.

A partly symmetric 25 bp lac operator fragment GGAATTGTGAGC<u>G</u>GATAACAATTCC (center of symmetry underlined; Seq. ID #26 nucleotides 20–44 of Seq. ID #16) from Pharmacia was inserted by blunt-end ligation into several positions relative to the T7 promoter (FIG. 2): the fragment was inserted into pET-7 in the filled-in BglII site ahead of base-pair −36, the filled-in AseI site ahead of −17, or the StuI site following +2, and into pET-7.1 in the StuI site following +8. The center of the lac operator is 13 bp from either end of the inserted fragment, which places it at base-pair −49, −30, +15 or +21 relative to the RNA start site at +1. Orientations were determined by sequencing each plasmid (Chen and Seeburg, 1985) with a primer directed toward the BamHI site of pBR322 (New England Biolabs). The rightward pointing arrow in FIG. 2 indicates that the operator sequence is oriented as written above, relative to the promoter sequence as given in the Figure. The nucleotide sequence from the RNA start of the promoter through the operator is given in FIG. 1 for the three promoter-operator combinations used most frequently: the T7lac promoter has a rightward operator centered on base-pair +15, the T7lacL promoter has a leftward operator at the same site, and the T7lac21 promoter has a rightward operator centered on base-pair +21.

EXAMPLE 2

Construction of T7 Lysozyme Plasmids

T7 gene 3.5, the gene for T7 lysozyme, was cloned in the BamHI site of pACYC184 (Chang and Cohen, 1978; Rose, 1988), a plasmid that is compatible with pBR322-based plasmids such as the pET plasmids. A fragment from plasmid pAR410 (Studier and Rosenberg, 1981: base-pairs 10,665 to 11,296 of T7 DNA) contains the coding sequence for the last 13 amino acids of T7 gene 3, the entire coding sequence of gene 3.5 (base-pairs 10,706 to 11,161), the φ3.8 promoter for T7 RNA polymerase, and the coding sequence for the first 24 amino acids of gene 3.8 (Dunn and Studier, 1983). Plasmid pLysE (Expressed) has this fragment oriented so that lysozyme mRNA is transcribed from the tet promoter of pACYC184; pLysS (Silent) has the fragment in the opposite orientation (FIG. 4). A shorter gene 3.5 fragment, which ends at base-pair 11,164 and therefore lacks the φ3.8 promoter and the beginning of gene 3.8, was also cloned. Plasmid pLysH (High level) has this shorter fragment oriented so that lysozyme mRNA is transcribed from the tet promoter; pLysL (Low level) has the fragment in the opposite orientation.

These lysozyme plasmids confer resistance to chloramphenicol; cells containing them are typically grown in medium containing 10 to 25 μg chloramphenicol/ml or are selected on plates to which 250 to 625 μg of chloramphenicol has been added to the top agar.

EXAMPLE 3

Lac-Repression In Vitro

In vitro transcription reactions (10 to 15 μl) contained 20 mM Tris-HCl (pH 7.6), 10 mM NaCl, 4 mM $MgCl_2$, 2 mM spermidine, 1 mM dithiothreitol, 0.4 mM each of GTP, CTP and UTP, 40 μM $[a^{-32}P]$ATP, and 1 to 4 nM template DNA. Where present, purified lac repressor (from Dr. Kathleen Matthews, Rice University, Houston, Tex.) was added at the indicated concentration and incubated at 37° C. for 10 minutes before addition of T7 RNA polymerase (100 nM). Where present, IPTG (1 mM) was added at the same time as lac repressor. Transcription was allowed to proceed for 20 minutes after T7 RNA polymerase was added, and then an equal volume of ice-cold 20 mM EDTA was added to stop the reaction. The samples were dried in a Speed-vac, resuspended in 90% (v/v) formamide, 0.1% (w/v) xylene cyanole FF, 0.1% (w/v) bromophenol blue, and subjected to electrophoresis through 12% (w/v) polyacrylamide sequencing gels. The labeled products were visualized by autoradiography.

The effect of purified lac repressor on transcription by T7 RNA polymerase from promoters having lac operators at different positions was examined as follows (FIG. 3). Transcription reactions were performed and analyzed in triplicate. The reactions contained no lac repressor, 70 nM repressor (1st three sets) or 140 nM repressor (last 2 sets), or lac repressor with 1 mM IPTG. The templates were plasmid DNAs that had been linearized by cutting with a restriction enzyme (NheI for the first four templates, EcoRV for the fifth). The T7 promoters were: the pET-7 promoter having an operator in the AseI site (centered at −30); the T7lacL promoter (operator centered at +15); the pET-7 promoter (no operator); the T7lac21 promoter (operator centered at +21); and the T7lac promoter (operator centered at +15). The predicted lengths of the runoff transcripts were 156, 181, 187 and 223.

EXAMPLE 4

Lac-Repression In vivo

Plasmids containing the T7lac, T7lacL and T7lac21 promoters

Plasmids equivalent to pET-7 with changes only in the T7 promoter region are referred to by the name of the promoter, e.g. pET-7.1, pT7lac, pT7lacL, etc. Plasmids that also contain the lacI gene are referred to by the name of the promoter followed by a number that identifies the specific configuration of elements in the plasmid (Table 2 and FIG. 9): odd-numbered plasmids have the lacI promoter directed away from the T7 promoter; even-numbered plasmids have both promoters directed toward the BamHI cloning site. The lacI gene on a BamhI fragment from pAR3712 was inserted into the SalI site of pT7lacL by blunt-end ligation of the filled-in ends to create pT7LacL-1 and pT7lacL-2; the other plasmids were derived from these.

Plasmid pT7lac21-1 was created by ligating the appropriate EcoNI-AvaI fragments from pT7lac21 and pT7lacL-1.

A second operator fragment was cloned into the trimmed SphI site of pT7lacL-1 and pT7lacL-2 to create pT7lacL-3 and pT7lacL-4, in which the second operator should be centered 238 bp upstream from the RNA start. The orientations of these second operators were not determined.

Derivatives that have the T7 transcription terminator Tφ located downstream from the BamHI cloning site were made by substituting the Tφ-containing PstI-BamHI fragment from pET-3 for the equivalent fragment in pT7lacL-1, -2, -3 and -4 to create pT7lacL-5, -6, -7 and -8.

The strong translation initiation region of T7 gene 10 (referred to as s10) was placed downstream from the T7lac promoter as follows. The ori-containing PstI-AvaI fragment of pT7lacL-2 was replaced by the equivalent fragment from pET-2c (which lacks the NdeI site at base-pair 2297 in pBR322) to create pAR4371. The pT7lac-2a, -b and -c translation vectors were created by three-fragment ligations (FIG. 10) of: (1) the lacI-containing PstI-SphI fragment from pAR4371; (2) the promoter-containing SphI to filled-in BstNI fragment from pT7lac; and (3) the PstI to filled-in XbaI fragment that contains the T7 gene 10 translation initiation region (s10) and the BamHI fusion cloning site from pET-2a, -b or -c. The blunt-end ligation between the filled-in XbaI and BstNI sites regenerated a unique XbaI site 41 bp upstream from the ATG initiation codon in these plasmids.

The orientation of the lacI gene was reversed by replacing the lacI-containing EcoNI-AvaI fragment of pT7lac-2a, -b and -c with the equivalent fragment from pT7lacL-1 to create pT7lac-1a, -b and -c. The pT7lac-3a, -b and -c and pT7lac-4a, -b and -c translation vectors, which carry a second operator centered 238 bp upstream from the RNA start, were created by replacing the small BglII-EcoNI fragment of pT7lac-1a, -b and -c, and pT7lac-2a, -b and -c with the equivalent, operator-containing fragment from pT7lacL-3. The relative positions and orientations of the promoter, operator(s) and lacI genes in the pT7lac-1, -2, -3 and -4 translation vectors are equivalent to those in the pT7lacL-1, -2, -3 and -4 transcription vectors (Table 2), except that the orientation of the operator centered at +15 is reversed between the transcription and translation vectors.

Plague Forming Assay

Phage lambda derivatives that carry and express T7 gene 1, the gene for T7 RNA polymerase, are prevented from growing when the host cell contains a multicopy plasmid that has a functional T7 promoter, apparently because active transcription of the plasmid by T7 RNA polymerase interferes with growth. Two such phages are DE2, in which gene 1 is transcribed from the $P_L$ and $P_I$ promoters, and DE3, in which gene 1 is transcribed from the lacUV5 promoter (Studier and Moffatt, 1986). Both phages make plaques with normal efficiency on HMS174/pBR322 but less than 1% efficiency on HMS174/pET-7 (Table 3). Thus, ability of DE2 or DE3 to form plaques provides a convenient test for whether a T7 promoter in a plasmid is functioning in the cell. (Inhibition of DE3 growth in the absence of inducer indicates that the cell does not contain enough lac repressor to repress completely the lacUV5 promoter in the phage DNA).

Neither DE2 nor DE3 formed plaques when the host carried pT7lacL (which does not carry lacI), confirming that the amount of lac repressor supplied by the chromosomal copy of lacI is insufficient to repress all of the operators on the multicopy plasmid. However, when HMS174 carried pT7lacL-1 or pT7lacL-2, which provide an additional source of lac repressor, both DE2 and DE3 gave plaques with normal efficiency in the absence but not in the presence of IPTG, clearly demonstrating that the T7lacL promoter is repressible by lac repressor and inducible by IPTG in vivo.

Even when repressed, the T7 promoters appeared to have some activity. DE2, which should produce the same high level of T7 RNA polymerase in the presence or absence of IPTG, gave plaques that were somewhat smaller than normal when the uninduced cells carried pT7lacL-2 and smaller still when they carried pT7lacL-1. The difference in plaque size between the two orientations of lacI in the plasmid may reflect a difference in the level of lac repressor. On the other hand, DE3 plaques appeared normal in both cases, indicating that sufficient lac repressor was present in either orientation to repress both the lacUV5 promoter that directs synthesis of T7 RNA polymerase from the phage DNA and the T7lacL promoter in the plasmid. This double repression reduced transcription by T7 RNA polymerase to the point where interference with plating behavior could no longer be detected.

It has been reported that a suitably spaced second operator can tighten repression of $E.$ $coli$ promoters (Mossing and Record, 1986; Hsieh et al., 1987; Oehler et al., 1990). To test whether this might also be the case with the T7lacL promoter, a second operator was inserted into pT7lacL-1 and pT7lac-2 so that it was centered 238 bp upstream from the RNA start site, generating plasmids pT7lacL-3 and pT7lacL-4. (The orientation of the second operator was not determined). The size of DE2 plaques on the uninduced cells increased in both cases (Table 3), so it seems likely that the second operator does tighten repression of the T7lacL promoter. DE2 gave apparently normal plaques on HMS174 that carried PT7lacL-4 and slightly smaller plaques when it carried pT7lacL-3, again suggesting a 35 difference in repression between the two orientations of lacI in the plasmid. The more than 100-fold reduction in plating efficiency in the presence of IPTG shows that the presence of the second operator does not prevent good induction of the T7 lacL promoter.

The T7lac21 promoter, where the operator is centered 6 bp further downstream from the RNA start, is less well repressed than the T7lacL promoter in vivo as well as in vitro: in contrast to pT7lacL-1, the presence of pT7lac21-1 did not permit plaque formation by DE2 in the absence of IPTG (Table 3). However, the combined repression of the polymerase gene in DE3 and the T7lac21 promoter in the plasmid reduced transcription sufficiently that DE3 gave normal plaques in the absence of IPTG.

Expression of the T7 Major Capsid (Gene 10) Protein

In BL21(DE3), the gene for T7 RNA polymerase is in the chromosome under control of the lacUV5 promoter (Studier and Moffatt, 1986). The plating behavior of DE2 and DE3 made it seem likely that the lacI gene in the pT7lacL plasmids would supply enough additional repressor that both the gene for T7 RNA polymerase and the T7lacL promoter in the plasmid would be well repressed.

The major capsid protein of T7, specified by gene 10, is produced in very large amounts from its natural $\phi$10 promoter in BL21(DE3) (Studier and Moffatt, 1986). Levels of expression of gene 10 protein were compared when the coding sequence was under control of its natural $\phi$10 promoter, the T7 promoter in pET-7, the T7lacL promoter in plasmids pT7lacL-1 or pT7lacL-2, or the T7lac21 promoter in pT7lac21-1 (FIG. 11). Cultures of BL21(DE3) were grown which contained gene 10 under control of its natural $\phi$10 promoter in plasmid pAR3625; the pET-7 promoter in plasmid pAR4367; the T7lacL promoter in pAR4348 (derived from pT7lacL-1, where the lacI promoter is directed away from gene 10); the T7lacL promoter in pAR4353 (derived from pT7lacL-2, where the lacI promoter is directed toward gene 10); and the T7lac21 promoter in pAR4442 (derived from pT7lac21-1). Proteins were labeled with [$^{35}$S]methionine immediately before, and 0.5, 1 and 1.5 hours after addition of rifampicin (200 $\mu$g/ml final concentration) and analysed by SDS-PAGE. Parallel samples from cultures labeled 1.5 hours after induction in the absence of rifampicin indicated the positions of the major gene 10 protein, 10A, and its frameshifted relative, 10B.

As shown in FIG. 11, considerable basal expression was apparent from the $\phi$10 or pET-7 promoters but very little from the T7lacL promoter in either pT7lacL-1 or pT7lacL-2. Basal expression from the less strongly repressed T7lac21 promoter was considerably higher than that from the T7lacL promoter but lower than that from the pET-7 promoter, which cannot be repressed. Upon induction, the rate of synthesis and total accumulation of gene 10 protein did not differ significantly among these plasmids.

Expression of $\beta$-Galactosidase

In order to quantify repressed and induced levels of expression from the lac-repressible promoters, the $\beta$-galactosidase (lacZ) gene was put under control of the T7 gene 10 translation signals and transcribed from the $\phi$10 promoter in pET-1b or from the T7lac promoter in pT7lac-1b, -2b, -3b or -4b (Table 4).

Plasmid pAR2197 expresses $\beta$-galactosidase under control of the T7 $\phi$10 promoter and gene 10 translation start. The lacZ coding sequence from codon 9 onward (from plasmid pMC1871: Casadaban et al., 1983) was fused at the BamHI site of pET-1b after the 13th codon from the gene 10 start. The coding sequence and translation initiation signals from this plasmid were placed under control of the T7lac promoter by ligating the lacZ-containing PstI-XbaI fragment from pAR2197 to the T7 lac-containing PstI-XbaI fragment from pT7lac-1b, -2b, -3b, and -4b.

Expression was measured in the lac deletion host BL26 (DE3) so that all $\beta$-galactosidase activity would arise from the plasmid being tested. The measured values are given for each sample without subtracting the value obtained for the host itself. A sample was assayed immediately before IPTG was added to half of each culture, and the parallel uninduced and induced cultures were assayed after one and two hours further incubation.

As expected from the results with gene 10 protein, the induced levels of $\beta$-galactosidase were similar from all five plasmids, but basal expression was much lower under control of the T7lac promoter than under control of the $\phi$10 promoter (Table 4). The results show a significant dependence on orientation of the lacI gene in the plasmid: pT7lac-1b and -3b, in which the lacI promoter is directed away from lacZ, had basal activities almost indistinguishable from background (perhaps 25 to 35% above it), whereas pT7lac-2b and -4b, in which the lacI promoter is directed toward lacZ, had basal activities about three to five times above background. Similar differences in basal activities were observed in BL26 itself, where no T7 RNA polymerase is present in the cell. Apparently, some transcription initiated by $E.$ $coli$ RNA polymerase at the lacI promoter continues past the T7lac promoter and through lacZ. The presence of the second operator upstream from the promoter in pT7lac- 3b and -4b seemed to have little effect on either basal or induced levels of β-galactosidase.

The effect of adding a compatible plasmid that supplies T7 lysozyme (pLysS) or additional lac repressor (pLacS) was also tested for each of these plasmids (Table 4). T7 lysozyme should reduce the basal activity by inhibiting T7 RNA polymerase, and indeed, the presence of pLysS reduced the basal activity arising from transcription from the φ10 promoter in pET-1b by about eight or ninefold. Even so, the basal activity remained about six to seven times background, higher than from any of the T7lac plasmids. However, pLysS did not provide a comparable reduction in basal level from any of the T7lac plasmids. The basal level from pT7lac-1b and -3b was already so close to background that any effect of pLysS would be difficult to detect. However, basal levels from pT7lac-2b and -4b were high enough that, if they were due to T7 RNA polymerase, an inhibition due to pLysS should have been detectable. The lack of an effect strengthens the argument that the higher basal levels from pT7lac-2b and -4b are due to transcription initiated at the lacI promoter by E. coli RNA polymerase, which would not be affected by T7 lysozyme.

The level of β-galactosidase induced after two hours was considerably reduced by the presence of pLysS. The presence of T7 lysozyme delays induction from the φ10 promoter and even more severely delays induction from T7lac (see Example 5 below). Levels would presumably have continued to rise if induction had been followed longer, but may not have reached the level produced in the absence of pLysS.

The additional lac repressor supplied by pLacs also reduced the basal activity from pET-1b by about eight- or ninefold. In this case, the added lac repressor must be acting to repress more strongly the lacUV5 promoter that directs transcription of the gene for T7 RNA polymerase in the chromosome, since no lac operator exists in the target plasmid. Full induction was seen without delay in the presence of pLacS, which suggests that this plasmid might be an attractive alternative to pLysS for reducing basal expression of target genes in some situations. The presence of pLacS had no detectable effect on basal or induced levels of β-galactosidase from the pT7 lac plasmids. Perhaps the lacI gene in these plasmids provides a nearly saturating amount of lac repressor, so that addition of pLacS has little further effect.

EXAMPLE 5

Sensitivity of Transcription From Different T7 Promoters to Inhibition by T7 lysozyme Expression of β-galactosidase from the T7lac promoter after induction of T7 RNA polymerase seems to be considerably more sensitive to inhibition by T7 lysozyme than is expression from the φ10 promoter (Table 4). The T7lac promoter is identical to the φ10 promoter upstream from the RNA start, and differs only in the transcribed region, beginning at base-pair +4 (FIG. 1). Transcription from at least some class II promoters of T7 DNA is also more sensitive to lysozyme inhibition.

Sensitivity to lysozyme inhibition is easily detected by following expression of T7 gene 10 protein from different T7 promoters upon induction of T7 RNA polymerase in BL21(DE3) or in BL21(DE3)pLysS, which supplies a low level of lysozyme. Different T7 promoters were tested in homologous plasmids in which the gene 10 coding sequence was preceded by 41 nucleotides of the natural sequence containing strong gene 10 translation signals and followed by the natural transcription terminator Tφ. The induction of gene 10 protein was analyzed by pulse labeling and SDS-PAGE. All of the promoters tested were essentially equivalent in expressing gene 10 protein upon induction in the absence of T7 lysozyme, but substantial differences were seen in the presence of lysozyme.

Similar to the observation with β-galactosidase, induction of gene 10 from the T7lacL promoter was much delayed relative to that from the φ10 promoter, presumably because a higher level of T7 RNA polymerase must accumulate before the lysozyme inhibition can be overcome. Expression from the pET-7 derivative was equally sensitive but expression from the pET-7.1 or T7lac21 promoters was little affected by T7 lysozyme. (Expression from the T7lac21 promoter was somewhat reduced in this experiment because about 25% of the cells had lost plasmid). Clearly, lysozyme sensitivity is not due simply to the presence of the lac operator or the lacI gene.

The relatively insensitive pET-7.1 and T7lac2 promoters have the entire conserved class III sequence (base-pairs −17 to +6), whereas the sensitive pET-7 and pT7lacL promoters differ from this sequence only in the base-pairs +3 to +6 (FIG. 1). The only difference in the entire plasmid between the pET-7 and pE-7.1 derivatives was the insertion of the sequence GAGAGG between the base-pairs +2 and +3 of the pET-7 promoter. Apparently, the nucleotide sequence of the transcribed region has an important effect on lysozyme sensitivity.

To test directly whether the differences from the conserved class III promoter sequences at base-pairs +3 and +4 of the T7lac and T7lacL promoters might be responsible for their increased sensitivity to T7 lysozyme, the sequence of base-pairs +1 through +6 in the relatively insensitive pET-7.1 promoter, GGGAGA, was changed to GGGGAA (the sequence in the sensitive T7lacL promoter) or to GGAGAA, creating the pET-7.2 and pET-7.3 promoters (FIG. 1 and Table 2). These changes caused little if any increase in sensitivity to lysozyme. Apparently, the increased sensitivity of the T7lac and T7lacL promoters also involves sequence differences beyond the conserved class III promoter sequence.

EXAMPLE 6

Cloning of T7 Autogenes

The T7 RNA polymerase gene was placed under the control of the repressible T7lacL promoter together with an adequate source of lac repressor. To create the appropriate plasmid, a PstI-BglII fragment that contains the coding sequence for T7 RNA polymerase, from plasmid pAR1173, was ligated to a PstI-BamHI fragment that contains the T7lacL promoter and the lacI gene, from pT7lacL-1. The lacI gene should provide enough lac repressor to saturate the T7lacL promoter in the multicopy plasmid, and the lacI promoter is oriented so as to direct transcription by E. coli RNA polymerase away from the gene for T7 RNA polymerase in the newly created plasmid (see pT7AUTO-1 in FIG. 4).

Since it was not known beforehand whether the repressed T7lacL promoter would reduce transcription by T7 RNA polymerase enough to allow such a plasmid to be established and maintained in E. coli, portions of the ligation mixture were used to transform not only HMS174 itself but also HMS174/pLysS. The compatible plasmid pLysS supplies a low level of T7 lysozyme.

Addition of IPTG, by unblocking the T7lacL promoter, might be expected to allow autocatalytic production of T7

RNA polymerase from the autogene and thereby prevent the host cell from forming a colony. By this test, none of six ampicillin-resistant transformants of HMS174 carried an autogene but 20 of 23 transformants of HMS174/pLyss did. The correctness of one of these plasmids, designated pT7AUTO-1 (Table 1 and FIG. 4), was confirmed by restriction analysis of the DNA.

A derivative of pT7AUTO-1 in which the gene for T7 RNA polymerase was followed by Tφ, the transcription terminator from T7 DNA, was prepared by ligating the appropriate PstI-BamHI fragments of pT7AUTO-1 and pET-3. The resulting plasmid, designated pT7AUTO-2 (Table 1 and FIG. 4), was also obtained upon transforming HMS174/pLysS but not HMS174 itself.

T7 RNA polymerase cloned under control of the T7lacL promoter in pT7AUTO-1 or pT7AUTO-2 is apparently not well enough shut off to avoid autocatalytic catastrophe except when the polymerase activity is reduced by the presence of T7 lysozyme. The requirement for T7 lysozyme was confirmed by attempting to transform HMS174, HMS174/pLysS, BL21 and BL21/pLysS with pT7AUTO-1 that had been prepared from HMS174/pLysS/pT7AUTO-1 and separated from the pLysS plasmid by gel electrophoresis. Many transformants were obtained when the recipient cells contained pLysS but only two each were obtained in HMS174 and BL21 themselves. All four of these latter transformants were also resistant to chloramphenicol, apparently because they were co-transformed by contaminating pLysS. Furthermore, pT7AUTO-1 could not be established in HMS174/pLacS, which supplies additional lac. Clearly, these autogene plasmids are difficult or impossible to establish in the absence of T7 lysozyme.

EXAMPLE 7

Expression of Fully Functional T7 RNA Polymerase From Autogenes

The inability of cells containing pT7AUTO-1 or pT7AUTO-2 to make colonies in the presence of IPTG suggests that transcriptionally active T7 RNA polymerase is produced from the T7 autogenes in these plasmids. A sensitive test for the presence of functional T7 RNA polymerase is the ability to support the growth of a T7 mutant that cannot provide its own RNA polymerase (Studier and Moffatt, 1986). T7 mutant 4107 lacks the gene for T7 RNA polymerase, is unable to acquire it from these plasmids by homologous genetic recombination, and is completely unable to form plaques unless the host cells supply active T7 RNA polymerase. This mutant forms plaques at normal efficiency on lawns of HMS174/pLysS carrying pT7AUTO-1 or pT7AUTO-2, demonstrating that the T7 RNA polymerase produced from these plasmids is functional. Since infection by the 4107 mutant would not be expected to lead to any increase in the amount of T7 RNA polymerase in the cell, the basal level present in cells containing pT7AUTO-1 or pT7AUTO-2 in the presence of pLysS must be high enough to support the growth of T7.

REFERENCES

Publications referred to in this application are listed here for easier access, since many of them are referred to several times in the text.

Ausubel, F. N., et al., eds., *Current Protocols in Molecular Biology*, New York: Greene Publishing Associates and Wiley Interscience.
Benton et al. (1990), *Mol. Cell, Biol.* 10:353–360.
Blackman, K., et al. (1976), *Proc. Nat. Acad. Sci., U.S.A.* 73:4174–4178.
Birnboim, H. C. and Doly, J. (1979), *Nucleic Acids Res.* 7:1513–1523.
Bolivar, F., et al. (1977), *Gene* 2:95–113.
Butler and Chamberlin (1982), *J. Biol. Chem.* 257:5772–5778.
Calos, M. P. (1978), *Nature (London)* 274:762–765.
Casababan, M. J., et al. (1983), *Methods Enzymol.* 100: 293–308.
Chamberlin, M., et al. (1970), *Nature (London)*, 228: 227–231.
Chang, A. C. Y. and Cohen, S. N. (1978), *J. Bacteriol.* 134:1141–1156.
Chapman, K. A. and Burgess, R. R. (1987), *Nucleic Acids Res.* 15:5413.
Chapman, K. A. and Wells, R. D. (1982), *Nucleic Acids Res.* 10(20):6331.
Chen, E. Y. and Seeburg, P. H. (1985), *DNA* 4:165–170.
Davanloo, P., et al. (1984), *Proc. Nat. Acad. Sci., U.S.A.* 81:2035–2039.
Deuschle, U., et al. (1986), *Proc. Nat. Acad. Sci., U.S.A.* 83:4134–4137.
Deuschle, U., et al. (1989), *Proc. Nat. Acad. Sci., U.S.A.* 86:5400–5404.
Dunaway, M., et al. (1980), *Proc. Nat. Acad. Sci., U.S.A.* 77:7181–7185.
Dunn, J. J., et al. (1971), *Nature New Biology* 230:94–96.
Dunn, J. J., et al. (1988), *Gene* 68:259–266.
Dunn, J. J. and Studier, F. W. (1983), *J. Mol. Biol.* 166:477–535; and erratum (1984), *J. Mol. Biol.* 175:111–112.
Fuerst, T. R., et al. (1986), *Proc. Nat. Acad. Sci., U.S.A.* 83:8122–8126.
Ghattas, I. R., et al. (1991), *Mol. Cell. Biol.* 11(12) :5848–5859.
Gilbert, W. and Maxam, A. (1973), *Proc. Nat. Acad. Sci. U.S.A.* 70:3581–3584.
Giordano, T. J., et al. (1989), *Gene* 84:209–219.
Golomb and Chamberlin (1974), *J. Biol. Chem.* 249:2858–2863.
Green et al. (1983), *Cell* 32:681–694.
Grodberg, J. and Dunn, J. J. (1988), *J. Bacteriol.* 170: 1245–1253.
Gunderson, S. I., et al. (1987), *Biochemistry* 26:1539–1549.
Hausmann (1976), *Current Topics in Microbiology and Immunology* 75:77–109.
Hsieh, W. T., et al. (1987), *J. Biol. Chem.* 262:14583–14591.
Ikeda, R. A. and Richardson, C. C. (1986), *Proc. Nat. Acad. Sci. U.S.A.* 83:3614–3618.
Inouye, M., et al. (1973), *J. Biol, Chem.* 248:7247–7252.
Jang, S. K. and Wimmer, E. (1990), *Genes & Development* 4:1560–1572.
Klement, J. F., et al. (1990), *J. Mol. Biol.* 215:21–29.
Korsten et al. (1975), *J. Gen. Virol.* 43:57–73.
Kotani, H., et al. (1987), *Nucl. Acids Res.* 15:2653–2664.
Kozak, M. (1989), *J. Cell Biol*, 108:229–241.
Kuhn, R., et al. (1990), *J. Virol.* [in press].
McAllister, W. T., et al. (1981), *J. Mol. Biol.* 153:527–544.
McAllister, W. T. and Carter, A. D. (1980), *Nucleic Acids Res.* 8(20):4821.
Moffatt, B. A. and Studier, F. W. (1987), Cell 49:221–227.
Morris, C. E., et al. (1986), *Gene* 41:193–200.

Mossing, M. C. and Record, M. T., Jr. (1986), *Science* 233:889–892.

Nakamura, K. and Inouye, M. (1982), *EMBO J.* 1:771–775.

Oehler, S., et al. (1990), *EMBO J.* 9:973–979.

Pelletier, J. and Sonenberg, N. (1988), *Nature* 334:320–325.

Pelletier, J. and Sonenberg, N. (1989), *J. Virol.* 63:441–444.

Rodriguez, D., et al. (1990), *J. Virol.* 64(10):4851–4857.

Rose, R. E. (1988), *Nucl. Acids Res.* 16:355.

Rosenberg, A. H., et al. (1987), *Gene* 56:125–135.

Schneider, T. D. and Stormo, G. D. (1989), *Nucleic Acids Res.* 17(2):659.

Schmitz, A. and Galas, D. J. (1979), *Nucl. Acids Res.* 6: 111–137.

Straney, S. B. and Crothers, D. M. (1987), *Cell* 51:699–707.

Studier, F. W. (1965), *J. Mol. Biol.* 1:373–390

Studier, F. W. and Rosenberg, A. H. (1981), *J. Mol. Biol.* 153:503–525.

Studier, F. W. and Moffatt, B. A. (1986), *J. Mol. Biol.* 189:113–130.

Studier, F. W., et A. (1990), *Methods Enzymol.* 15: 60–89.

Tabor, S. and Richardson, C. C. (1985), *Proc. Nat. Acad. Sci., U.S.A.* 82:1074–1078.

Towie et al. (1975), *J. Biol. Chem.* 250:1723–1733.

Trono, D., et al. (1988), *J. Virol.* 62:2291–2299.

Wensink, P. C., et al. (1974), *Cell* 3:315–325.

Zinn et al. (1983), *Cell* 34:865–879.

TABLE 1

Plasmids containing T7 autogenes

| Plasmid | Promoter | Coding sequence | Terminator |
|---|---|---|---|
| pT7AUTO-1 | T7lacL | T7 RNA polymerase | |
| pT7AUTO-2 | T7lacL | T7 RNA polymerase | Tφ |
| pT7AUTO-3 | T7lac21 | T7 RNA polymerase | |
| pT7AUTO-4 | T7lac21 | T7 RNA polymerase | Tφ |

TABLE 2

Plasmids containing the T7lac, T7lacL, or T7lac21 promoters

| Plasmid | Orientation of lacI[a] | Upstream operator | Elements downstream from BamHI cloning site[b] |
|---|---|---|---|
| pT7lac | | | |
| pT7lacL | | | |
| pT7lacL-1 | O | | |
| pT7lacL-2 | S | | |
| pT7lacL-3 | O | −238 | |
| pT7lacL-4 | S | −238 | |
| pT7lacL-5 | O | | Tφ BglII AvaI BglII |
| pT7lacL-6 | S | | Tφ BglII AvaI BglII |
| pT7lacL-7 | O | −238 | Tφ BglII AvaI BglII |
| pT7lacL-8 | S | −238 | Tφ BglII AvaI BglII |
| pT7lac21 | | | |
| pT7lac21-1 | O | | |

[a]The lacI promoter transcribes in the same (S) or opposite (O) direction as the T7 promoter.
[b]The downstream BglII-AvaI-BglII sites arose because two BglII linkers were inserted downstream from Tφ in the precursor to pET-3.

TABLE 3

Plating of DE2 and DE3 on HMS174 containing plasmids with different T7 promoters

| | Orienta-tion of lacI[a] | Upstream operator | Plating efficiency[b] Uninduced | | +IPTG |
|---|---|---|---|---|---|
| Plasmid | | | DE2 | DE3 | DE2 or DE3 |
| pBR322 | | | 1.0 N | 1.0 N | 1.0 N |
| pET-7 | | | <0.01 | <0.01 | <0.01 |
| pT7lacL | | | <0.01 | <0.01 | <0.01 |
| pT7lacL-1 | O | | 1.0 S | 1.1 N | <0.01 |
| pT7lacL-2 | S | | 1.2 SN | 1.4 N | <0.01 |
| pT7lacL-3 | O | −238 | 1.2 SN | 1.3 N | <0.01 |
| pT7lacL-4 | S | −238 | 1.5 N | 1.4 N | <0.01 |
| pT7lac21 | | | <0.01 | <0.01 | <0.01 |
| pT7lac21-1 | O | | <0.01 | 1.0 N | <0.01 |

[a]The lacI promoter transcribes in the same (S) or opposite (O) direction as the T7 promoter.
[b]The plating efficiency of DE2 or DE3 relative to that on HMS174/pBR322 is given. Where IPTG was present, 2.5 μmol was added to the top agar. Sizes of the plaques are indicated as normal (N), somewhat smaller than normal (SN), or small (S).

TABLE 4

β-Galactosidase levels from different plasmids in BL26(DE3)

| Plasmid containing lacZ | Additional plasmid | Relative level of β-galactosidase activity[a] Uninduced | | | +IPTG | |
|---|---|---|---|---|---|---|
| | | 0 | 1 h | 2 h | 1 h | 2 h |
| None | | 180 | 140 | 150 | 140 | 140 |
| | pLysS | 140 | 140 | 120 | 130 | 120 |
| | pLacS | 170 | 170 | 150 | 160 | 160 |
| pET-1b (φ10) | | 7000 | 6200 | 5800 | 27,000 | 44,000 |
| | pLysS | 780 | 860 | 970 | 9,100 | 19,000 |
| | pLacS | 950 | 810 | 860 | 25,000 | 52,000 |
| pT7lac-1b | | 250 | 160 | 200 | 12,400 | 30,000 |
| | pLysS | 180 | 160 | 150 | 1,440 | 5,000 |
| | pLacS | 220 | 210 | 200 | 14,000 | 31,000 |
| pT7lac-2b | | 390 | 440 | 550 | 28,000 | 42,000 |
| | pLysS | 520 | 650 | 830 | 3,900 | 6,500 |
| | pLacS | 650 | 600 | 730 | 15,400 | 32,000 |
| pT7lac-3b | | 250 | 160 | 170 | 8,500 | 25,000 |
| | pLysS | 190 | 140 | 140 | 1,600 | 5,100 |
| | pLacS | 220 | 200 | 210 | 11,000 | 25,000 |
| pT7lac-4b | | 500 | 410 | 540 | 9,500 | 25,000 |
| | | 480 | 500 | 670 | 1,200 | 2,100 |
| | | 490 | 490 | 570 | 8,800 | 23,000 |

[a]β-Galactosidase activity was measured essentially as described by Miller (1972), but with no correction of $A_{420}$ for light-scattering of the sample. Cultures were grown at 37° C. in M9 medium plus appropriate antibiotic(s) until the $A_{600}$ reached 0.4 to 0.5. Activity was assayed on 50 μl of uninduced or 5 μl of induced culture immediately before and 1 and 2 hours after half of each culture was induced by 0.4 mM IPTG. The values in the Table were calculated by multiplying the $A_{420}$ value by 1000 and dividing by the product of the incubation time (10 minutes), the volume of culture assayed (0.05 or 0.005 ml), and the $A_{600}$ value of the culture at the time of the assay.

Equivalents

Those skilled in the art will know, or be able to ascertain using no more than routine experimentation, many equivalents to the specific embodiments of the invention described herein. These and all other equivalents are intended to be encompassed by the following claims.

We claim:

1. An autogene, comprising a gene encoding a T7-like bacteriophage RNA polymerase under the control of an autogene promoter recognized by said polymerase.

2. An autogene, comprising a gene encoding bacteriophage T7 RNA polymerase under the control of an autogene promoter recognized by said polymerase.

3. The autogene of claim 1, wherein said bacteriophage is selected from the group consisting of:
   a) *Escherichia coli* phages T7, T3, φI, φII, W31, H, Y, A1122, cro, C21, C22, and C23;
   b) *Pseudomonas putida* phage gh-1;
   c) *Salmonella typhimurium* phage SP6;
   d) *Serratia marcescens* phage IV;
   e) Citrobacter phage ViIII; and
   f) Klebsiella phage Number 11.

4. The autogene of claim 1, wherein the autogene promoter is selected from the group consisting of:
   a) a naturally occurring bacteriophage promoter; and
   b) a naturally occurring bacteriophage promoter having an alteration which changes the strength of the promoter relative to that of the wild type promoter, but is still recognized by said polymerase.

5. The autogene of claim 2, wherein the autogene promoter recognized by T7 RNA polymerase is selected from the group consisting of:
   a) a naturally occurring class III promoter;
   b) a naturally occurring class II promoter; and
   c) a naturally occurring T7 promoter having an alteration in the −17 to +6 region.

6. The autogene of claim 5, wherein the autogene promoter is the T7 φ10 promoter whose DNA sequence differs from natural T7 class III promoters by containing AG instead of GA at positions +4 and +5, where +1 is the transcriptional start site.

7. The autogene of claim 1, wherein the autogene promoter is regulatable and comprises:
   a) a promoter which is recognized by the autogene-encoded RNA polymerase; and
   b) the binding site of a DNA-binding protein;
wherein binding of said DNA-binding protein interferes with transcription from said autogene promoter.

8. The autogene of claim 7, wherein the binding site is the lac operator.

9. The autogene of claim 8, wherein the autogene promoter is recognized by T7 RNA polymerase and the lac operator is centered at a position from +12 to +21 relative to the transcriptional start site.

10. The autogene of claim 9, wherein the autogene promoter comprises a sequence selected from the group consisting of:
   a) TAATACGACTCACTATAGGGGAATTGT-GAGCGGATAACAATTCC (Seq. ID #27; nucleotides 1–44 of Seq. ID #6);
   b) TAATACGACTCACTATAGGGGAATTGT-TATCCGCTCACAATTCC (Seq. ID #28; nucleotides 1–44 of Seq. ID #7);
   c) TAATACGACTCACTATAGGGAATTGT-GAGCGGATAACAATTCC (Seq. ID #10);

d) TAATACGACTCACTATAGGGAATTGT-TATCCGCTCACAATTCC (Seq. ID #11);
e) TAATACGACTCACTATAGGAATTGT-GAGCGGATAACAATTCC (Seq. ID #12);
f) TAATACGACTCACTATAGGAATTGT-TATCCGCTCACAATTCC (Seq. ID #13);
g) TAATACGACTCACTATAGAATTGT-GAGCGGATAACAATTC (Seq. ID # 14);
h) TAATACGACTCACTATAGAATTGTTATC-CGCTCACAATTC (Seq. ID #15); and
i) TAATACGACTCACTATAGGGAGAGGG-GAATTGTGAGCGGATAACAATTCC (Seq. ID #29; nucleotides 1–50 of Seq. ID #8).

11. A construct for expressing the RNA polymerase of a T7-like bacteriophage, comprising:
a) an autogene, which comprises a gene encoding a T7-like bacteriophage RNA polymerase under the control of an autogene promoter recognized by said polymerase; and
b) a vector appropriate for maintenance of the construct in a host cell.

12. The construct of claim 11, wherein the T7-like bacteriophage is selected from the group consisting of:
a) *Escherichia coli* phages T7, T3, φI, φII, W31, H, Y, A1122, cro, C21, C22, and C23;
b) *Pseudomonas putida* phage gh-1;
c) *Salmonella typhimurium* phage SP6;
d) *Serratia marcescens* phage IV;
e) Citrobacter phage ViIII; and
f) Klebsiella phage Number 11.

13. The construct of claim 11, wherein the autogene promoter is regulatable and comprises:
a) a promoter which is recognized by the autogene-encoded RNA polymerase; and
b) the binding site of a DNA-binding protein;
wherein binding of said DNA-binding protein interferes with transcription from said autogene promoter.

14. The construct of claim 13, wherein the autogene promoter is recognized by T7 RNA polymerase and the binding site is the lac operator, wherein the lac operator is centered at a position from +12 to +21 relative to the transcriptional start site.

15. The construct of claim 13, further comprising a sequence selected from the group consisting of:
a) a lacI gene under the control of a second promoter;
b) the T7 transcriptional terminator Tφ placed downstream of the autogene; and
c) combinations of these.

16. The construct of claim 15, wherein the second promoter is the natural promoter of the lacI gene.

17. The construct of claim 15, wherein the lacI gene is transcribed in the opposite direction from the autogene.

18. The construct of claim 15, which is selected from the group consisting of:
a) pT7AUTO-1;
b) pT7AUTO-2;
c) pT7AUTO-3; and
d) pT7AUTO-4.

19. An expression system for producing T7 RNA polymerase in host cells, comprising:
a) an autogene construct, comprising:
1) an autogene, which comprises a gene encoding T7 RNA polymerase under the control of an autogene promoter comprising:
a) a promoter recognized by said polymerase; and
b) the lac operator, wherein the lac operator is centered at a position from +12 to +21 relative to the transcriptional start site; and
2) the lacI gene under the control of a second promoter; and
b) a lysozyme construct, comprising a T7 lysozyme gene under the control of a third promoter.

20. The system of claim 19, wherein the autogene and lysozyme constructs, respectively, are selected from the group consisting of:
a) pT7AUTO-1 and pLysL;
b) pT7AUTO-2 and pLysS;
c) pT7AUTO-1 and pLysS;
d) pT7AUTO-2 and pLysE;
e) pT7AUTO-3 and pLysE;
f) pT7AUTO-1 and pLysE;
g) pT7AUTO-1 and pLysH; and
h) pT7AUTO-2 and pLysH.

21. A method for producing T7 RNA polymerase in host cells, comprising the steps of:
a) providing host cells;
b) providing the expression system of claim 19;
c) introducing the expression system into the host cells, thereby producing host cells containing the expression system; and
d) inducing expression of the autogene, thereby producing host cells expressing T7 RNA polymerase;
thereby producing T7 RNA polymerase.

22. The method of claim 21, wherein the autogene and lysozyme constructs, respectively, are selected from the group consisting of:
a) pT7AUTO-1 and pLysL;
b) pT7AUTO-2 and pLysS;
c) pT7AUTO-1 and pLysS;
d) pT7AUTO-2 and pLysE;
e) pT7AUTO-3 and pLysE;
f) pT7AUTO-1 and pLysE;
g) pT7AUTO-1 and pLysH; and
h) pT7AUTO-2 and pLysH.

23. The host cells obtained in step c) of claim 21.

24. The method of claim 21, further comprising isolating the T7 RNA polymerase from the host cells produced in step d).

25. A method for producing an autogene, comprising:
a) providing a first DNA fragment that contains the complete coding sequence for the RNA polymerase of a T7-like bacteriophage but no promoter that is recognized by said RNA polymerase;
b) providing a second DNA fragment that contains a promoter that is recognized by said bacteriophage RNA polymerase; and
c) joining said first and second DNA fragments so as to place the coding sequence for said bacteriophage RNA polymerase under control of said promoter that is recognized by said bacteriophage RNA polymerase, producing an autogene.

26. The method of claim 25, wherein said bacteriophage is selected from the group consisting of:
(a) *Escherichia coli* phages T7, T3, φI, φII, W31, H, Y, A1122, cro, C21, C22, and C23;
(b) *Pseudomonas putida* phage gh-1;

(c) *Salmonella typhimurium* phage SP6;

(d) *Serratia marcescens* phage IV;

(e) Citrobacter phage ViIII; and (f) Klebsiella phage Number 11.

27. The method of claim 25, wherein the autogene promoter is selected from the group consisting of:
- (a) a naturally occurring bacteriophage promoter; and
- (b) a naturally occurring bacteriophage promoter having an alteration which changes the strength of the promoter relative to that of the wild type promoter, but is still recognized by said polymerase.

28. The method of claim 25, wherein the bacteriophage is T7 and the autogene promoter recognized by T7 RNA polymerase is selected from the group consisting of:
- (a) a naturally occurring class III promoter;
- (b) a naturally occurring class II promoter; and
- (c) a naturally occurring T7 promoter having an alteration in the −17 to +6 region.

29. The method of claim 25, wherein the method further comprises:
providing a third DNA fragment encoding a binding site of a DNA-binding protein; and
inserting the binding site into the autogene such that binding of the DNA-binding protein to the binding site interferes with transcription from said autogene promoter.

30. The method of claim 25, wherein the method further comprises modifying the first DNA fragment so as to change the efficiency of translation of the coding sequence for the RNA polymerase in a host cell.

31. An autogene produced by the method of claim 30, wherein the efficiency of translation of the coding sequence for the RNA polymerase in a host cell is decreased.

32. An autogene produced by the method of claim 30, wherein the efficiency of translation of the coding sequence for the RNA polymerase in a host cell is increased.

* * * * *